(12) United States Patent
Gibson et al.

(10) Patent No.: US 12,371,724 B2
(45) Date of Patent: *Jul. 29, 2025

(54) METHODS FOR IN VITRO JOINING AND COMBINATORIAL ASSEMBLY OF NUCLEIC ACID MOLECULES

(71) Applicant: Codex DNA, Inc., San Diego, CA (US)

(72) Inventors: Daniel G. Gibson, Crofton, MD (US); Hamilton O. Smith, San Diego, CA (US); Clyde A. Hutchison, La Jolla, CA (US); Lei Young, Gaithersburg, MD (US); J. Craig Venter, La Jolla, CA (US)

( * ) Notice: Subject to any disclaimer, the term of this patent is extended or adjusted under 35 U.S.C. 154(b) by 214 days.

This patent is subject to a terminal disclaimer.

(21) Appl. No.: 17/877,657

(22) Filed: Jul. 29, 2022

(65) Prior Publication Data

US 2022/0364134 A1   Nov. 17, 2022

Related U.S. Application Data

(60) Continuation of application No. 16/388,722, filed on Apr. 18, 2019, now Pat. No. 11,408,020, which is a
(Continued)

(51) Int. Cl.
*C12P 19/00* (2006.01)
*C12N 9/00* (2006.01)
(Continued)

(52) U.S. Cl.
CPC ............. *C12P 19/34* (2013.01); *C12N 9/22* (2013.01); *C12N 9/93* (2013.01); *C12N 15/10* (2013.01);
(Continued)

(58) Field of Classification Search
None
See application file for complete search history.

(56) References Cited

U.S. PATENT DOCUMENTS 6,183,960 B1   2/2001   Lizardi
6,379,964 B1   4/2002   Del Cardayre et al.
(Continued)

FOREIGN PATENT DOCUMENTS

WO   WO 98/38297 A1   9/1998
WO   WO 2007/029144 A2   2/2007
WO   WO 2007/032837 A2   3/2007

OTHER PUBLICATIONS

Coco et al., "*DNA Shuffling Method for Generating Highly Recombined Genes and Evolved Enzymes*,"; Nature Biotechnol. (2001), 19:354-359, Nature Publishing Group.
(Continued)

*Primary Examiner* — Aaron A Priest

(57) ABSTRACT

The present invention relates to methods of joining two or more double-stranded (ds) or single-stranded (ss) DNA molecules of interest in vitro, wherein the distal region of the first DNA molecule and the proximal region of the second DNA molecule of each pair share a region of sequence identity. The method allows the joining of a large number of DNA fragments, in a predetermined order and orientation, without the use of restriction enzymes. It can be used, e.g., to join synthetically produced sub-fragments of a gene or genome of interest. Kits for performing the method are also disclosed. The methods of joining DNA molecules may be used to generate combinatorial libraries useful to generate, for example, optimal protein expression through codon optimization, gene optimization, and pathway optimization.

20 Claims, 14 Drawing Sheets

Specification includes a Sequence Listing.

Related U.S. Application Data continuation of application No. 14/636,082, filed on Mar. 2, 2015, now Pat. No. 10,266,865, which is a division of application No. 12/371,543, filed on Feb. 13, 2009, now Pat. No. 8,968,999.

(60) Provisional application No. 61/142,101, filed on Dec. 31, 2008, provisional application No. 61/098,202, filed on Sep. 18, 2008, provisional application No. 61/052,614, filed on May 12, 2008, provisional application No. 61/029,312, filed on Feb. 15, 2008, provisional application No. 61/064,107, filed on Feb. 15, 2008.

(51) Int. Cl.

| | |
|---|---|
| *C12N 9/22* | (2006.01) |
| *C12N 15/10* | (2006.01) |
| *C12N 15/64* | (2006.01) |
| *C12N 15/66* | (2006.01) |
| *C12P 19/34* | (2006.01) |

(52) U.S. Cl.
CPC ......... *C12N 15/1027* (2013.01); *C12N 15/64* (2013.01); *C12N 15/66* (2013.01)

(56) References Cited

U.S. PATENT DOCUMENTS

| | | |
|---|---|---|
| 6,458,544 B1 | 10/2002 | Miller |
| 6,821,758 B1 | 11/2004 | Koltermann et al. |
| 7,723,077 B2 | 5/2010 | Young et al. |
| 8,440,404 B2 | 5/2013 | Makarov et al. |
| 8,936,937 B2 | 1/2015 | Lindbo |
| 2004/0191871 A1 | 9/2004 | Hyman |
| 2005/0164213 A1* | 7/2005 | Tabor ............... C12Q 1/6844 435/6.1 |
| 2005/0202490 A1 | 9/2005 | Makarov et al. |
| 2007/0037196 A1* | 2/2007 | Gibson ............... C12N 15/10 435/5 |
| 2007/0037197 A1 | 2/2007 | Young et al. |
| 2010/0071085 A1 | 3/2010 | Lindbo |

OTHER PUBLICATIONS

Coljee et al., "*Seamless Gene Engineering Using RNA- and DNA-Overhang Cloning,*"; Nature Biotechnol. (2000), 18:789-791, Nature America Inc.

Extended European Search Report issued on Jul. 18, 2016, regarding EP 16165528.7.

European Patent Office Communication issued on Aug. 19, 2013, regarding EP 09711127.2.

Gibson et al., "*Complete Chemical Synthesis, Assembly, and Cloning of a Mycoplasma genitalium Genome.*"; Science (2008), 319(5867):1215-1220, Blackwell Science Ltd.

Gibson et al., "*Enzymatic Assembly of DNA Molecules up to Several Hundred Kilobases,*"; Nature Methods (2009), 6(5):343-345 + Methods, Nature America, Inc.

Moretti et al., "*Enhancement of PCR Amplification Yield and Specificity Using AmpliTaq GoldTM DNA Polymerase*"; BioTechniques 25:716-722 (Oct. 1998).

Walker et al., "*Isothermal in vitro Amplification of ONA by a Restriction Enzyme/DNA Polymerase System,*"; Proc. Natl. Acad. Sci. USA (1992) 89:392-396.

\* cited by examiner

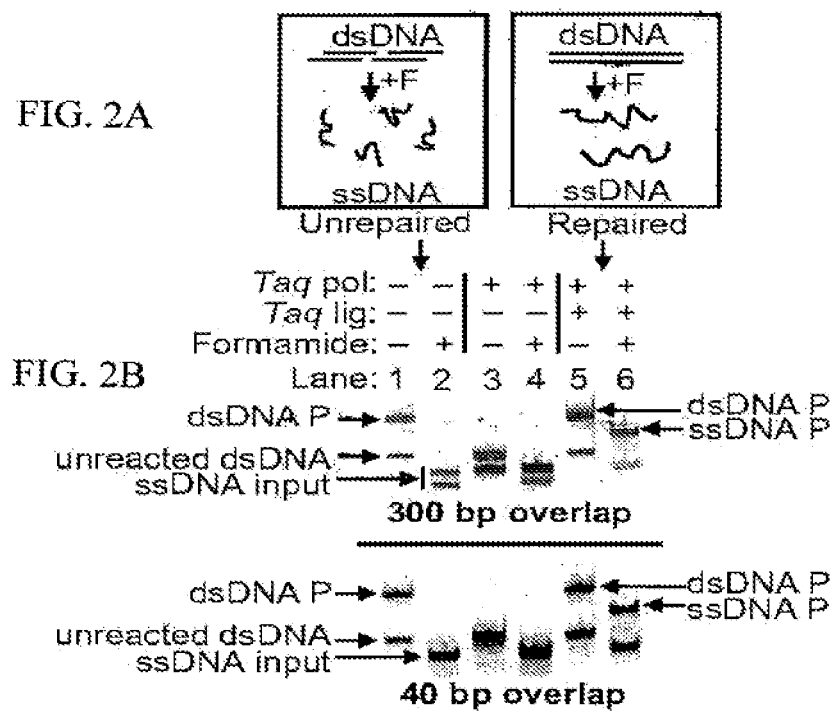
FIG. 2A
FIG. 2B
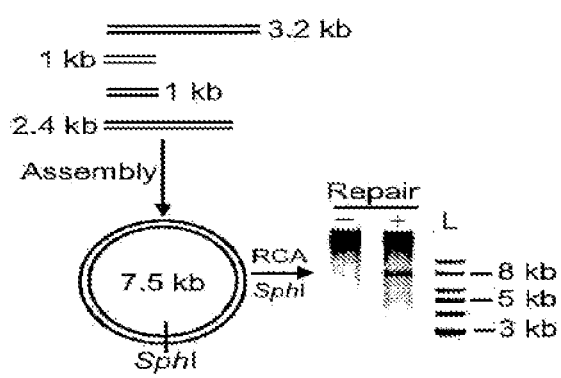
FIG. 3

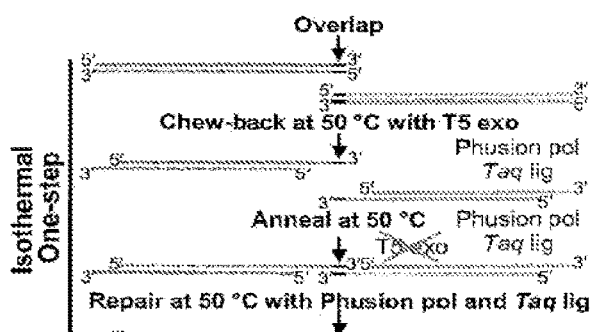
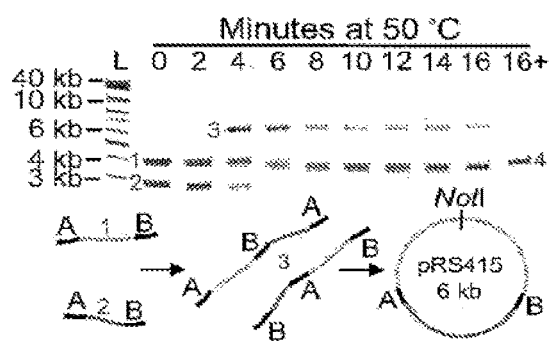
FIG. 5A
FIG. 5B
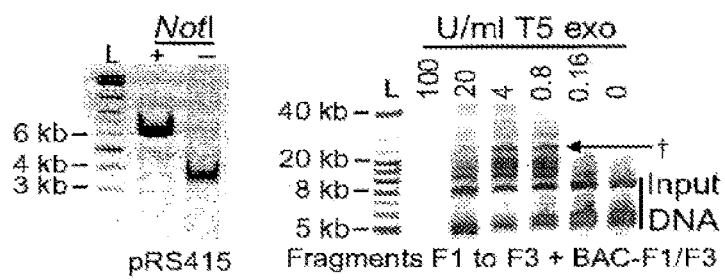
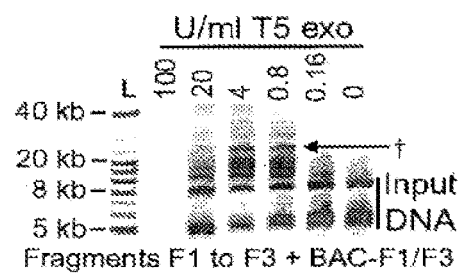
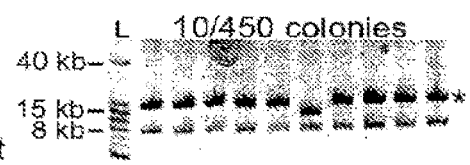
FIG. 5C
FIG. 5D
FIG. 5E

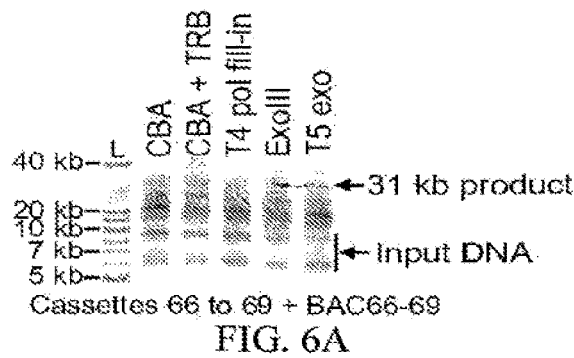
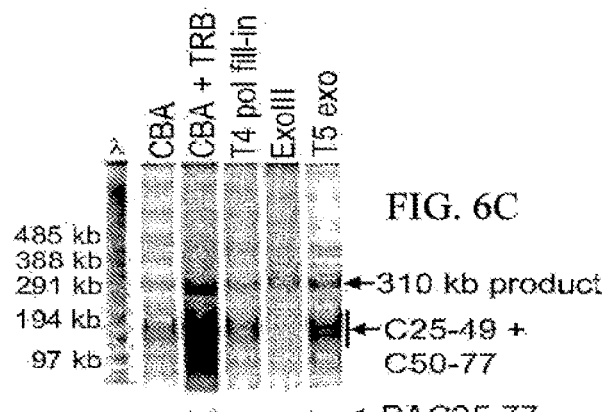
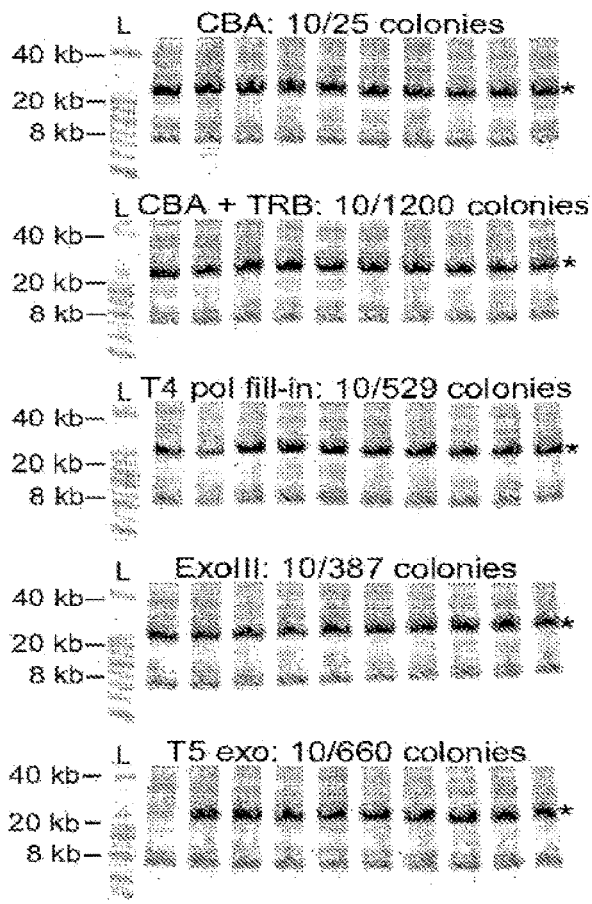
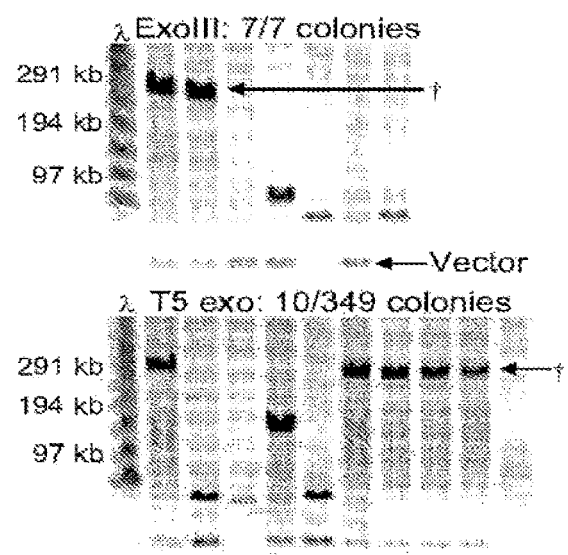
FIG. 6A
FIG. 6B
FIG. 6C
FIG. 6D

METHODS FOR IN VITRO JOINING AND COMBINATORIAL ASSEMBLY OF NUCLEIC ACID MOLECULES

CROSS-REFERENCE TO RELATED APPLICATIONS

This application is a continuation application of U.S. application Ser. No. 16/388,722 filed Apr. 18, 2019, now issued as U.S. Pat. No. 11,408,020; which is a continuation application of U.S. application Ser. No. 14/636,082 filed Mar. 2, 2015, now issued as U.S. Pat. No. 10,266,865; which is a divisional application of U.S. application Ser. No. 12/371,543 filed Feb. 13, 2009, now issued as U.S. Pat. No. 8,968,999; which claims the benefit under 35 USC § 119(e) to U.S. Application Ser. No. 61/142,101 filed Dec. 31, 2008, U.S. Application Ser. No. 61/098,202 filed Sep. 18, 2008, U.S. Application Ser. No. 61/052,614 filed May 12, 2008, U.S. Application Ser. No. 61/064,107 filed Feb. 15, 2008 and U.S. Application Ser. No. 61/029,312 filed Feb. 15, 2008. The disclosure of each of the prior applications is considered part of and is incorporated by reference in the disclosure of this application.

INCORPORATION BY REFERENCE OF SEQUENCE LISTING

The material in the accompanying sequence listing is hereby incorporated by reference into this application. The accompanying sequence listing text file, named CODEX1290-8_ST26.xml, was created on Jul. 25, 2022 and is 22 kB in size. The file can be accessed using Microsoft Word on a computer that uses Windows OS.

BACKGROUND OF THE INVENTION

Field of the Invention

The invention concerns methods for in vitro joining of single-stranded and/or double-stranded nucleic acid molecules permitting efficient one-step assembly of multiple nucleic acid molecules with overlapping terminal sequences. Invention methods are particularly useful in effecting systematic combinatorial assembly of fragments of nucleic acid sequence variants to modify properties of the joined nucleic acid sequence, for example, nucleic acid sequences providing variants of codon usage, control sequences, genes, pathways, chromosomes, extra-chromosomal nucleic acids, and genomes.

Background Information

A two-step thermocycler-based method was used to assemble portions of the *M. genitalium* genome, as described in Gibson, D. G., el al., "Complete chemical synthesis, assembly, and cloning of a *Mycoplasma genitalium* genome." *Science* (2008) 319:1215-1220. Another approach is described by Li, M. Z., et al., *Nature Meth.* (2007) 4:251-256. A single-step method of assembly employing T7 5' exonuclease and single-stranded DNA binding protein is disclosed in PCT publication WO2006/021944. The present invention discloses one-step procedures which facilitate assembly of DNA molecules in vitro. These methods employ either a non-thermostable 5' exonuclease that lacks 3' exonuclease activity or a 3' exonuclease that is functional in the presence of dNTPs.

These new methods are particularly useful in an additional aspect of the invention which provides systematic combinatorial assembly to modify nucleic acid molecules. Combinatorial techniques for assembly of chemical compounds for use in high throughput screening is by now well established. In addition, gene shuffling techniques in which coding sequences are randomly fragmented and reannealed have been practiced for a number of years. For instance, protocols to create libraries of chimeric gene fragments are described in Meyer, M., et al, "Combinatorial Recombination of Gene Fragments to Construct a Library of Chimeras" *Current Protocols in Protein Science* (2006) 26.2.1-26.2.17; McKee, A. E., et al., *JBEI* abstract. There is, however, a need for a systematic approach to combinatorial approach that does not rely on random rearrangement or shuffling to provide optimized nucleic acid sequences, for example, with optimized coding sequences or metabolic pathways, that can be selected according to desired properties. The present invention fills this need by providing a systematic combinatorial approach to assemble a variety of nucleic acids of interest.

Techniques for assembling various components into complete or minimal genomes have been established. For example, U.S. Patent Publication 2000/0264688, published 15 Nov. 2007, describes methods for constructing a synthetic genome by generating and assembling cassettes comprising portions of the genome. A stepwise hierarchical method to assemble nucleic acids is described in U.S. Patent Publication 2007/004041, published 4 Jan. 2007. However, no suggestion is made of using these techniques systematically to assemble a desired nucleic acid molecule.

It is understood that construction of a genome need not include all of the components that occur naturally. PCT Publication WO2007/047148 describes a minimal genome based on *Mycoplasma genitalium* wherein as many as 101 genes encoding proteins can be omitted and still retain viability. There is no suggestion that the components of the minimal genome be systematically assembled as combinatorial libraries permitting the formation of a multiplicity of alternative minimal genomes.

The present invention, thus, is directed to systematic methods and the products thereof that permit efficient and extensive modification of nucleic acid molecules to provide and screen nucleic acid assemblies of interest in a high-throughput manner, and readily adaptable to robotic implementation. In alternative embodiments, assembly reactions can be performed on a solid surface as opposed to in a reaction tube, for example, on a chip using microfluidics (such as shown in Huang, Y., et al., *Lab Chip* (2007) 7:24-26).

The techniques for systematic combinatorial assembly of nucleic acids representing variant coding sequences, expression systems, pathway synthesis and minimal or larger genomes employ in vitro assembly techniques at least in part. Any suitable in vitro assembly technique may be employed; however, the methods of the present invention include improvements on those already described in the art.

SUMMARY OF THE INVENTION

In a first aspect, the invention provides an in vitro method of joining a set of two or more double-stranded (ds) or single-stranded (ss) DNA molecules. The adjacent DNA molecules to be joined contain overlapping sequences at their termini. The two or more DNA molecules are contacted in vitro in a single vessel with (a) an isolated non-thermostable 5' to 3' exonuclease that lacks 3' exonuclease activity, (b) a crowding agent, (c) an isolated thermostable non-strand-displacing DNA polymerase with 3' exonuclease activity, or a mixture of said DNA polymerase with a second DNA polymerase that lacks 3' exonuclease activity, (d) an isolated thermostable ligase, (e) a mixture of dNTPs, and (f) a suitable buffer, under conditions that are effective for joining the two or more DNA molecules to form a first assembled dsDNA molecule in a one-step reaction.

In some embodiments, the exonuclease of (a) is a T5 exonuclease and the contacting is under isothermal conditions, and/or the crowding agent of (b) is PEG, and/or the non-strand-displacing DNA polymerase of (c) is PHUSION® DNA polymerase or VENT$_R$® DNA polymerase, and/or the ligase of (d) is Taq ligase.

In some embodiments, the conditions are also suitable for digesting any unpaired, non-homologous, single-stranded DNAs following the joining reaction. At least some of the DNA molecules to be joined comprise, at one terminus, a sequence that is non-homologous to any of the DNA molecules of interest. Optionally, the non-homologous sequences comprise one or more binding regions for PCR primers, and/or regions of homology to vector sequences, and/or recognition sites for one or more restriction enzymes that are not present within the DNA molecules of interest, e.g., rare-cutting restriction enzymes.

The method may be employed to join a second set of two or more DNA molecules to one another to obtain a second assembled DNA molecule in addition to a first assembled molecule, and the first and the second assembled DNA molecules joined to obtain a third assembled ds DNA molecule. This process may be sequentially repeated as required to obtain the whole nucleic acid sequence of interest.

The invention also provides kits for performing the above methods that comprise: (a) an isolated non-thermostable 5' to 3' exonuclease that lacks 3' exonuclease activity, (b) a crowding agent, (c) an isolated thermostable non-strand-displacing DNA polymerase with 3' exonuclease activity, or a mixture of said DNA polymerase with a second DNA polymerase that lacks 3' exonuclease activity, and (d) an isolated thermostable ligase, in appropriate amounts. For example, the kit may contain T5 exonuclease, PEG, PHUSION® DNA polymerase, and Taq ligase.

In a second aspect, the invention is directed to an alternative in vitro method of joining a set of two or more double-stranded (ds) or single-stranded (ss) DNA molecules, where adjacent DNA molecules to be joined contain overlapping sequences at their termini. The method comprises contacting in vitro the two or more DNA molecules in a single vessel with (a) an isolated non-thermos table 3' to 5' exonuclease active in the presence of dNTPs, (b) a crowding agent, (c) an isolated heat-activated DNA polymerase, (d) an isolated thermostable ligase, (e) a mixture of dNTPs, and (f) a suitable buffer, under conditions that are effective for joining the two or more DNA molecules to form a first assembled dsDNA molecule in a one-step thermocycled reaction.

In one embodiment of this aspect, the exonuclease of (a) is Exonuclease III, and/or the polymerase of (c) is heat-activated by the removal of an inactivating moiety combined with the polymerase in a heat-sensitive manner; and/or the crowding agent of (b) is PEG, and/or the ligase of (d) is Taq ligase. The DNA polymerase of (c) may be AMPLITAQ GOLD®.

This method may also be employed to obtain a second assembled set of DNA molecules that can be combined with a first assembled set. Any combination of the thermocycled one-step method and the foregoing isothermal method may be used for assembly of various sets of DNA molecules and any of the two may be used for subsequent assembly of larger DNA molecules from the assembled sets.

The components for the above method may be provided as a kit that comprises, in a single vessel: (a) an isolated non-thermostable 3' to 5' exonuclease active in the presence of dNTPs, (b) a crowding agent, (c) an isolated heat-activated DNA polymerase, (d) an isolated thermostable ligase, (e) a mixture of dNTPs, and (f) a suitable buffer, in amounts such that when said two or more DNA molecules are added to the kit, in the presence of a suitable buffer solution and dNTPs, and incubated under thermocycled conditions, the two or more DNA molecules are assembled in a concerted reaction. In one embodiment of this aspect, the kit comprises: (a) Exonuclease III, (b) PEG, (c) AMPLITAQ GOLD® DNA polymerase, and (d) Taq ligase.

Any combination of materials useful in the disclosed methods of the first and second aspects can be packaged together as a kit for performing any of the disclosed methods. For example, a kit can comprise a mixture containing all of the reagents necessary for assembling ssDNA molecules (e.g., oligonucleotides) or dsDNA molecules.

In a third aspect, the invention provides a method of modifying the properties of a whole nucleic acid molecule. The method comprises: (a) representationally dividing the nucleic acid sequence of said whole nucleic acid molecule into a multiplicity of portions along its length thereby identifying the sequences of partial nucleic molecules; (b) providing, for at least 3 of said partial nucleic molecules, a multiplicity of variants of each partial nucleic acid molecule; (c) combinatorially assembling in vitro said variants along with any partial nucleic acid molecules which are not varied, wherein the partial nucleic acid molecules or variants thereof contain overlapping sequences at their termini whereby assembly of the partial nucleic acid molecules and variants thereof in the mixture would result in assembly of a multiplicity of variants of the whole nucleic acid molecule; and (d) expressing the variants of the whole nucleic acid molecule to determine any modified properties of said variants of said whole nucleic acid molecule.

The assembling of step (c) may be performed by either of the foregoing methods, although alternative joining methods may also be used. Multistep in vitro methods may be used, for example, or in vivo methods, such as those described in PCT application PCT/US2008/079109 (WO 2009/048885) may be used. While in vitro assembly methods are generally more convenient for oligonucleotides, in vivo assembly methods are also workable alternatives.

One assembly method that may be employed comprises the steps of: (a) contacting said variants along with any partial nucleic acid molecules which are not varied with a non-processive 5' exonuclease; and with (b) a single stranded DNA binding protein (SSB) which accelerates nucleic acid annealing; and with (c) a non-strand-displacing DNA polymerase; and with (d) a ligase, under conditions effective to join the variants and partial nucleic acid molecules that are not varied so as to result in assembly of a multiplicity of variants of the whole nucleic acid molecule.

This aspect, in one embodiment, comprises dividing the nucleic acid sequence of the whole nucleic acid molecule into at least 5 portions which can advantageously be assembled using the in vitro methods of the invention. In other embodiments, the partial nucleic acid molecular variants provide degenerate forms of the codon for one or more amino acids encoded by the partial nucleic acid molecules. Alternatively, the variants of the partial nucleic acid molecule provide a multiplicity of nucleic acid control sequences affecting transcription or translation of the whole nucleic acid molecule. As another alternative, the variants of the partial nucleic acid molecule provide a multiplicity of regions encoding domains or motifs of peptides or proteins encoded by the whole nucleic acid molecule. As yet another alternative, the peptides or proteins encoded by said partial nucleic acid molecules function together in a metabolic pathway.

The various recombination approaches set forth above can be used to construct any desired assembly, such as plasmids, vectors, genes, metabolic pathways, minimal genomes, partial genomes, genomes, chromosomes, extrachromosomal nucleic acids, for example, cytoplasmic organelles, such as mitochondria (animals), and in chloroplasts and plastids (plants), and the like. For the assembly of large DNA molecules, the final steps may be conducted in vivo, where yeast is a preferred host. The balance between in vitro and in vivo conduct of assembly steps is determined by the practicality of the method with regard to the nature of the DNA molecules to be assembled.

The invention further includes libraries of DNA molecules obtained by the foregoing methods, and methods to use the modified whole DNA molecules. The libraries, which contain 2 or more variants, but typically multiple variants, such as 20, 100, 1000 or more can be screened for members having desired characteristics, such as high production levels of desired products, enhanced functionality of the products, or decreased functionality (if that is advantageous). Such screening may be done by high throughput methods, which may be robotic/automated.

The invention also further includes products made by the methods of the present invention, for example, the resulting assembled synthetic genes or genomes and modified optimized genes and genomes, and the use and products thereof.

The recombinant methods of the invention have a wide variety of applications, permitting, for example, the design of pathways for the synthesis of useful products, including pharmaceuticals, biofuels, diagnostics, veterinary products, agricultural chemicals, growth factors, and the like—i.e., any molecule that can be assembled in a cell culture or in a transgenic animal or plant. As a simple example, the acetate pathway of *E. coli* can be adapted to produce biofuels such as ethanol, butanol and the like. Enzymes on a synthetic pathway for a secondary metabolite, such as a polyketide, can also be optimized using the methods of the invention. Thus, the DNA molecules that result from the systemic combinatorial procedures of the invention may be employed in a wide variety of contexts to produce useful products.

BRIEF DESCRIPTION OF THE DRAWINGS

FIG. 2A is a schematic of the strategy used to analyze the success of a repaired assembly reaction. dsDNA is denatured to ssDNA in the presence of formamide (+F), and ssDNA remains intact with a higher molecular weight if repair has occurred.

FIG. 2B shows the results of the method of FIG. 2A used to analyze products assembled using the method shown in FIG. 1A.

FIG. 3 shows the results of rolling circle amplification (RCA) of repaired assembly products joining 4 DNA fragments, showing that only repaired assembly products are amplified.

FIG. 5A is a schematic of a one-step isothermal in vitro assembly using T5 exonuclease.

FIG. 5B shows the results of assembly of 2 nucleic acid fragments, 4,024 bp and 2,901 bp, with ~450 bp overlapping sequences, using the method shown in FIG. 5A, and incorporating a NotI restriction enzyme sequence.

FIG. 5C shows the results of NotI digestion of the product shown in FIG. 5B.

FIG. 5D shows the results of assembly of 3 nucleic acid fragments, each ~5 kb, together with a vector sequence of ~8 kb, with 40 bp overlapping sequences, using the method shown in FIG. 5A.

FIG. 5E shows representative results of DNA purified from *E. coli* transformed with the assembly product shown in FIG. 5D, and digested with Not I to release the assembled fragments from the vector.

FIGS. 6A-6D show the results of direct comparisons of the methods shown in FIG. 1A (T4 polymerase), FIG. 4A (exonuclease III) and FIG. 5A (T5 exonuclease).

FIG. 6A shows the results of assembly of 4 nucleic acid fragments, 5.9 kb to 6.2 kb, with 80 bp overlapping sequences, together with a vector of ~8 kb with 80 bp overlapping sequences, using the various assembly methods described above.

FIG. 6B shows representative results of DNA purified from *E. coli* transformed with the assembly products shown in FIG. 6A, and digested with NotI to release the assembled fragments from the vector.

FIG. 6C shows the results of assembly of 2 one-quarter genomes of *Mycoplasma genitalium*, together with a vector of ~8 kb with 80 bp overlapping sequences, using the various assembly methods described above.

FIG. 6D shows representative results of DNA purified from *E. coli* transformed with the assembly products shown in FIG. 6C, and digested with NotI to release the assembled fragments from the vector.

FIG. 9A shows the results of assembly of five 300 bp fragments, in 15 reactions covering the entire mouse mitochondrial genome.

FIG. 9B shows the results of amplification of the reaction products shown in FIG. 9A.

FIG. 9C shows the results of assembly of five 1,180 bp products of the reaction shown in FIG. 9A, in 3 reactions covering the entire mouse mitochondrial genome.

FIG. 9D shows the results of amplification of the reaction products shown in FIG. 9C.

FIG. 9E shows the results of the final assembly of the whole mouse mitochondrial genome from three 5,560 bp products of the reaction shown in FIG. 9C, in a vector construct.

FIG. 9F shows the results of the final assembly of the whole mouse mitochondrial genome product shown in FIG. 9F after removal of the vector sequence and recircularization.

DETAILED DESCRIPTION OF THE INVENTION

Modes of Carrying Out the Invention

Definitions

Figure 1A:
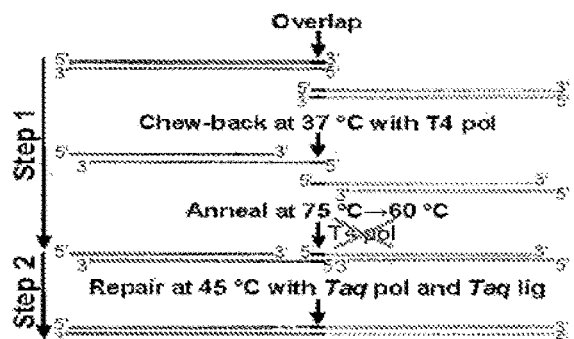
FIG. 1A is a schematic of a two-step thermocycled in vitro assembly using T4 polymerase.

As used herein, the singular forms "a," "an," and "the" include plural referents unless the context clearly dictates otherwise.

The term "about," as used herein, refers to plus or minus 20%. Thus, "about" 30 minutes includes 24-30 minutes. "About" also refers to plus or minus 20% when referring to lengths of nucleic acids, temperatures, etc. The end points of ranges, as used herein, are included in the range. When plus or minus 20% results in a non-integral value of indivisible units, such as nucleotides, a skilled worker will recognize that one should round the value to the nearest integer. For example, about 8 nucleotides is not 6.4 to 9.6 nucleotides, but should be interpreted as 6 to 10 nucleotides.

The term "activity temperature" refers to the temperature above which the DNA polymerase is sufficiently more active than the exonuclease (i.e., exonuclease III) such that there is a net reduction in the length of the single-strand overhangs created initially by the exonuclease (i.e., exonuclease III).

In those methods of the invention that are carried out "in vitro", all of the protein components are isolated and/or substantially purified. The in vitro assembly reactions are not carried out in a living cell or with a crude cell extract; the reactions are carried out in a cell-free environment.

The "joining" of DNA molecules by a method of the invention is sometimes referred to herein as "recombination" or "assembly" of the DNA molecules.

According to the present invention, optimization at the genetic level is achieved in a systematic manner by design of discrete components. This is true at all levels of combination as described above. The invention methods thereby avoid the random nature of prior art approaches.

Methods of Nucleotide Assembly

In brief, when the DNA molecules to be joined are double-stranded, the preferred method comprises incubating the DNA molecules with (a) an exonuclease (e.g., a non-processive exonuclease), which "chews-back" the ends of the double-stranded DNA molecules, to expose single-stranded overhangs comprising the regions of overlap; (b) a crowding agent, such as PEG, which, among other functions, accelerates nucleic acid annealing, so that the single-stranded overhangs are annealed (hybridized) specifically; (c) a non-strand-displacing DNA polymerase, which fills in remaining single-stranded gaps in the annealed molecules, by extending the 3' ends of the annealed regions; and (d) a thermostable ligase, which seals (ligates) the nicks thus formed. For single-stranded molecules, the exonuclease of (a) may be, but need not be, omitted.

When the DNA molecules to be joined are single-stranded, the single-stranded DNA molecules (e.g., oligonucleotides of about 40-60 bases, also referred to herein as nucleotides or nt) anneal via the sequences of identity at their ends (e.g., about 20 bases), to form gapped molecules. The exonuclease activity may act on these gapped molecules to increase the size of the gap. The gapped molecules are then repaired with the polymerase and the ligase, as above, to form double stranded molecules.

The novel one-step methods of the invention can be used to simultaneously join a large number of DNA molecules. To accomplish this, the DNA molecules to be joined are designed so that, for each pair of DNA molecules to be joined contain overlapping sequences at their termini—i.e., the distal region of one DNA molecule comprises a region of unique sequence homology (e.g., identity) with the proximal region of the other DNA molecule. Distal and proximal refer to an arbitrary reference point at one end of a chain of molecules, e.g., with respect to the referent X,

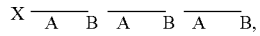

A represents a proximal and B represents a distal region. To facilitate the joining of the DNA molecules in a predetermined orientation and order, each set of distal and proximal regions of sequence identity is selected (designed) to be unique (to be different from the regions of sequence identity of the other pairs of DNA molecules). The method allows a number of DNA molecules to be joined in a single reaction mixture, and in a single vessel. It will be evident that the regions of homology are, in some circumstances, complementary. The term a "region of sequence identity" encompasses both identical and complementary sequences.

In methods of the invention, the distal region of one of a pair of dsDNA molecules to be joined shares a region of sequence homology (e.g., sequence identity) with the proximal region of the other dsDNA molecule. The term "distal" as used herein refers to the 3' end of a first DNA molecule of a pair to be joined (the 5'-most DNA molecule), and the term "proximal" refers to the 5' end of the second DNA molecule of the pair. The regions of homology are sometimes referred to herein as "overlaps", "overlapping sequences", or "regions of overlap." A "region of sequence homology (identity)", as used herein, refers to both strands of the double-stranded DNA molecule. Thus, one strand from this region can hybridize specifically to its complementary strand, e.g., when the complementary regions are present in single-stranded overhangs from the distal and proximal regions of the two molecules to be joined.

In one embodiment, the DNA molecules which are joined are synthetically generated DNA molecules that may lie adjacent to one another in a gene or genome of interest. For example, a first set of about eight 60-mer single-stranded oligonucleotides (oligos) having 20 base regions of sequence identity at either end may be joined in the proper order and orientation to form a dsDNA of 300 bp. A second set of a similar number of adjoining DNA molecules of about the same size may also be joined; and then, in a second stage assembly, the two sets of joined molecules are joined to one another. The process is repeated with further sets of DNA molecules, in as many cycles as desired. In such a manner, the component elements of a gene or genome, all or nearly all of which have been generated synthetically, can be joined in sequential steps to form a complete gene or genome.

Advantages of the method of the invention include the ability to perform the joining reactions under well-defined conditions, using well-characterized, isolated (e.g., substantially purified) enzymes. This allows the joining reactions to be controlled and reproducible. In a method of the invention, the joining process is not subject to competing reactions brought about by other enzymes in the reaction mixture, such as exonucleases and endonucleases which can be present in cells or cell extracts. The joining methods of the invention are accurate, inexpensive, require very little sample handling, and can be completed rapidly (e.g., between about 15 minutes and an hour, such as between about 15 and about 30 minutes) in single vessel. If desired, the steps of the method can be carried out robotically, without the intervention of an investigator.

Other advantages of a method of the invention include the following: the ability to join DNA molecules in a defined order and orientation allows, for example, for the cloning of one or more fragments of interest into a linearized vector in a defined orientation; or for the assembly of component DNA portions of a longer sequence of interest (such as the assembly of component parts of a synthetic gene or genome); or for the assembly and cloning of sub-fragments of a DNA which are too large to clone using a PCR amplification step. The method allows one to join and/or clone DNA molecules of interest without having to rely on the presence of restriction enzyme recognition sites at the ends of the fragments to be joined. The in vitro procedure also allows one to assemble DNAs that are unstable or otherwise recalcitrant to in vivo cloning, and thus would be difficult to clone by a method requiring transformation into and replication in a bacterium. If desired, DNAs assembled by a method of the invention can then be amplified in vitro (e.g., by multiple displacement amplification (MDA), such as rolling circle amplification (RCA); or by PCR), again without having to passage the DNA through a bacterium. If desired, DNA molecules can be assembled in the presence of vector, so that the cloned sequence can be transformed into a suitable host cell directly after the assembly is complete.

These methods can be repeated sequentially, to assemble larger and larger molecules. For example, a method of the invention can comprise repeating a method as above to join a second set of two or more DNA molecules of interest to one another, and then repeating the method again to join the first and second set DNA molecules of interest, and so on. At any stage during these multiple rounds of assembly, the assembled DNA can be amplified by transforming it into a suitable microorganism, or it can be amplified in vitro (e.g., with PCR or rolling circle amplification (RCA)).

In one aspect of the invention, the DNA molecules of interest are single-stranded oligonucleotides that are about 40-60 bases in length, and the region of sequence identity consists of no more than 20 bases. In other aspects of the invention, the DNA molecules of interest are double-stranded DNA molecules of at least about 100, 200, 500, 1,000, 5,000, 50,000, 100,000, 200,000, 500,000, or $1\times10^6$ bp in length. The regions of sequence identity in these dsDNA molecules may comprise at least about 20, 30 or 40 nucleotides (nt), e.g., at least about 80, 300, 500 or more nt.

The methods of the invention may be used to join at least about 8 DNA oligonucleotides (oligos), e.g., as many as about 100 oligonucleotides in a single concerted reaction, to generate one contiguous DNA. In a single vessel, many such concerted reactions can take place simultaneously. For example, in a single vessel, hundreds of reactions can be performed simultaneously, in each of which 8 oligonucleotides are assembled to form a contiguous DNA, resulting in hundreds of contiguous DNAs. For the joining of dsDNA molecules in a single concerted reaction, there may at least about 4 (e.g., at least about 5, 10, 25, 50, 75 or 100 molecules), wherein for each pair of molecules to be joined, the distal region of one DNA molecule comprises a region of sequence homology to the proximal region of the other DNA molecule, and each set of distal and proximal regions of homology is unique for each pair of DNA molecules to be joined.

In a joining reaction of the invention, the collection of DNA molecules of interest to be joined can further comprise a linearized vector DNA molecule, and the joined DNAs of interest can thus be cloned into the vector. Such molecules can, if desired, be transformed into a host cell (e.g., a microorganism, such as a bacterium (e.g., *E. coli*), yeast or a eukaryotic cell, such as a mammalian cell).

In methods of the invention, one or more (e.g., all) of the DNA molecules can be generated synthetically. The DNA molecules may be adjacent sequences of a gene or genome of interest. In one embodiment, the DNA molecules are synthesized so as to comprise overlapping regions of sequence identity at their ends, and the DNA molecules are joined to form part or all of a synthetic gene or genome.

In one aspect of the invention, each of the DNA molecules of interest to be joined comprises, at the free end of each of the two regions of identity, a sequence that is non-homologous to any of the DNA molecules of interest; and during the joining reaction, the non-homologous sequences are removed by the 3' exonuclease activity of the polymerase (for the isothermal method) or the 5' exonuclease activity of the polymerase for the thermocycled method. The non-homologous sequences may comprise one or more binding domains for PCR primers (e.g., four different binding domains), and/or recognition sites for one or more restriction enzymes.

Thus, methods of the invention can be readily adapted to be automated and high throughput (e.g., carried out by robotic methods).

Chew-Back

In methods of the invention, the exonuclease digestion is carried out under conditions that are effective to chew-back a sufficient number of nucleotides to allow for specific annealing of the exposed single-stranded regions of homology. In general, at least the entire region of overlap is chewed back, leaving overhangs which comprise the region of overlap. In some methods, the exonuclease digestion may be carried out by a polymerase in the absence of dNTPs (e.g., T5 DNA polymerase) while in other methods, the exonuclease digestion may be carried out by an exonuclease in the presence of dNTPs that lacks polymerase activity (e.g., exonuclease III).

In other embodiments, e.g., when the region of overlap is very long, it may only be necessary to chew-back a portion of the region (e.g., more than half of the region), provided that the single-stranded overhangs thus generated are of sufficient length and base content to anneal specifically under the conditions of the reaction. By "annealing specifically" is meant herein that a particular pair of single-stranded overhangs will anneal preferentially (or only) to one another, rather than to other single-stranded overhangs which are present in the reaction mixture. By "preferentially" is meant that at least about 95% of the overhangs will anneal to the paired overhang. A skilled worker can readily determine the optimal length for achieving specific annealing of a sequence of interest under a given set of reaction conditions. Generally, the homologous regions of overlap (the single-stranded overhangs or their complements) contain identical sequences. However, partially identical sequences may be used, provided that the single-stranded overhangs can anneal specifically under the conditions of the reactions.

Crowding Agent

A suitable amount of a crowding agent, such as PEG, in the reaction mixture allows for, enhances, or facilitates molecular crowding. Without wishing to be bound by any particular mechanism, it is suggested that a crowding agent, which allows for molecular crowding, binds to and ties up water in a solution, allowing components of the solution to come into closer contact with one another. For example, DNA molecules to be recombined can come into closer proximity; this thus facilitates the annealing of the single-stranded overhangs. Also, it is suggested that enzymes can come into closer contact with their DNA substrates and can be stabilized by the removal of water molecules. A variety of suitable crowding agents will be evident to the skilled worker. These include a variety of well-known macromolecules, such as polymers, e.g., polyethylene glycol (PEG); FICOLL®, such as FICOLL® 70; dextran, such as dextran 70; or the like. Much of the discussion in this application is directed to PEG. However, the discussion is meant also to apply to other suitable crowding agents. A skilled worker will recognize how to implement routine changes in the method in order to accommodate the use of other crowding agents.

In general, when PEG is used, a concentration of about 5% (weight/volume) is optimal. However, the amount of PEG can range, e.g., from about 3 to about 7%. Any suitable size of PEG can be used, e.g., ranging from about PEG-200 (e.g., PEG-4000, PEG-6000, or PEG-8000) to about PEG-20,000, or even higher. In the Examples herein, PEG-8000 was used. The crowding agent can, in addition to enhancing the annealing reaction, enhance ligation.

Gap Repair

Following the annealing of single stranded DNA (either overhangs produced by the action of exonuclease when the DNA molecules to be joined are dsDNA, or the regions of sequence identity of single stranded DNA molecules when the DNAs to be joined are single-stranded DNA), the single-stranded gaps left by the exonuclease are filled in with a suitable thermostable, non-strand-displacing, DNA polymerase (sometimes referred to herein as a "polymerase") and the nicks thus formed a sealed with a thermostable ligase. A "non-strand-displacing DNA polymerase," as used herein, is a DNA polymerase that terminates synthesis of DNA when it encounters DNA strands which lie in its path as it proceeds to copy a dsDNA molecule, or that degrades the encountered DNA strands as it proceeds while concurrently filling in the gap thus created, thereby generating a "moving nick" (nick translation).

The nicks generated by the gap-filling reaction can be sealed with any of a variety of suitable thermostable DNA ligases (sometimes referred to herein as "ligases"). Among the suitable ligases are, for example, Taq ligase, Ampligase Thermostable DNA ligase (Epicentre Biotechnologies), the Thermostable ligases disclosed in U.S. Pat. No. 6,576,453, Thermostable Tfi DNA ligase from Bioneer, Inc., etc.

Generally, substantially all of the nicks (or all of the nicks) are sealed during the reaction procedure. However, in one embodiment, joined DNA which still comprises some nicks can be transformed into a bacterium, such as E. coli, where the nicks are sealed by the bacterial machinery.

The amount of the enzymes used in a method of the invention can be determined empirically. Generally, the amount of 5' exonuclease activity is substantially lower than the amount of the polymerase activity, and ligase activity is in large excess over the polymerase. Suitable amounts of enzymes to be used in a method of the invention are illustrated in the Examples herein.

Reaction components (such as salts, buffers, a suitable energy source (such as ATP or NAD), pH of the reaction mixture, etc.) that are present in a reaction mixture of the invention may not be optimal for the individual enzymes (exonuclease, polymerase and ligase); rather, they serve as a compromise that is effective for the entire set of reactions. Some exemplary reaction conditions are presented in the Examples. For example, one suitable buffer system identified by the inventors, sometimes referred to herein as ISO (ISOthermal) Buffer typically comprises 0.1 M Tris-Cl pH 7.5; 10 mM $MgCl_2$, 0.2 mM each of dGTP, dATP, dTTP and dCTP, 10 mM DTT, 5% PEG-8000, and 1 mM NAD.

In a method of the invention, the proteins having exonuclease, polymerase and ligase activities are isolated (e.g., substantially purified); cell extracts or intact cells are not employed. The term, an "isolated" protein, as used herein, means that the protein is removed from its original environment (e.g., the natural environment if it is naturally occurring), and isolated or separated from most other component with which it is naturally associated. For example, a naturally-occurring protein present in its natural living host (e.g., a bacteriophage protein present in a bacterium that has been infected with the phage) is not isolated, but the same protein, separated from some or all of the coexisting materials in the natural system, is isolated. Such proteins can be part of a composition or reaction mixture, and still be isolated in that such composition or reaction mixture is not part of its natural environment. The term "an isolated protein," as used herein, can include 1, 2, 3, 4 or more copies of the protein, i.e., the protein can be in the form of a monomer, or it can be in the form of a multimer, such as dimer, trimer, tetramer or the like, depending on the particular protein under consideration. In some embodiments, the protein is purified. Methods for purifying the proteins used in methods of the invention are conventional. In some embodiments, the protein is substantially purified or is purified to homogeneity. By "substantially purified" is meant that the protein is separated and is essentially free from other proteins, i.e., the protein is the primary and active constituent. The purified protein can then be contacted with the DNAs to be joined. Proteins used in the methods of the invention can be in the form of "active fragments," rather than the full-length proteins, provided that the fragments retain the activities (enzymatic activities or binding activities) required to achieve the joining. One of skill in the art will recognize how to make and use such active fragments.

Joining DNA Molecules

In methods of the invention, at least two DNA molecules are contacted with the enzymes under conditions effective to join the DNA molecules to form a substantially intact (preferably having no nicks) double-stranded DNA molecule (e.g., in which a single copy of the region of sequence identity is retained).

A method of the invention can be used to join any DNA molecules of interest, including DNAs which are naturally occurring, cloned DNA molecules, synthetically generated DNAs, etc. The joined DNA molecules may, if desired, be cloned into a vector (e.g., using a method of the invention).

DNA molecules of any length can be joined by methods of the invention. Single-stranded oligonucleotides of about 40-60 bases can be joined, e.g., via overlaps of about 20 bases. The minimum size for joining molecules with a 40 bp overlap is about 80 bp. For molecules with a 200 bp overlap, the minimum size is about 400 bp. Theoretically, there should be no maximum size of DNA molecules that can be joined (although very large molecules would be more fragile than smaller ones, and thus subject to possible breakage). For example, cassettes having about 100 bp to about 750 or 1,000, or more, can be joined.

From two to an essentially unlimited upper level of DNA molecules can be joined. In general, at least about 5-10 fragments can be joined. The number of fragments which can be joined depends, in part, on the length of the overlaps and the lengths of the fragments. For example, with fragments having overhangs of about 150 to about 200 bp (e.g., fragments of about 3 kb, or larger or smaller), the number of fragments that can be joined is substantially unlimited. The number of fragments that can be joined in one reaction also depends, in part, on the efficiency of the joining process. If the efficiency of joining is 100%, then an infinite number of DNA molecules could theoretically be joined (provided that an approximately equal number of molecules of each substrate is present in the reaction). With lower efficiencies (e.g., about 75-90% joining of each pair of two molecules), two to about 250 DNA molecules can be joined. Methods of the invention work well with a wide range of substrate DNA (e.g., about 10 to about 1,000 ng of each substrate in a reaction mixture.)

In some embodiments of the invention, the joined DNA molecules form a circle and/or become ligated into a vector to form a circle. The lower size limit for a dsDNA to circularize is about 200 base pairs. Therefore, the total length of the joined fragments (including, in some cases, the length of the vector) is preferably at least about 200 bp in length. There is no practical upper size limit, and joined DNAs of a few hundred kilobase pairs, or larger, can be generated by a method of the invention. The joined DNAs can take the form of either a circle or a linear molecule.

More particularly, the number of DNA molecules or cassettes that may be joined in vitro to produce an end product, in one or several assembly stages according to the invention, may be at least or no greater than about 2, 3, 4, 6, 8, 10, 15, 20, 25, 50, 100, 200, 500, 1,000, or 10,000 DNA molecules, for example in the range of about 4 to about 100 molecules. The number of assembly stages may be about 2, 4, 6, 8, 10, or more. The number of molecules assembled in a single stage may be in the range of about 2 to about 10 molecules. The methods of the invention may be used to join together DNA molecules or cassettes each of which has a starting size of at least or no greater than about 40 bs, 60 bs, 80 bs, 100 bs, 500 bs, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of about 3 kb to about 500 kb. The DNA end products of the inventive methods may be at least about 500 bs, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of 30 kb to 1 Mb. In one embodiment, the inventive methods are used for the in vitro assembly of short single-stranded oligonucleotides, through several rounds of assembly, into cassettes of about 6 kb, and then the assembly of 100 such cassettes into a DNA molecule of about 600 kb.

When joining a mixture of DNA molecules, it is preferable that the DNAs be present in approximately equimolar amounts. If the number of DNA molecules is not balanced, the result would be a termination of assembled species. For example, consider an example in which 8 DNA molecules are to be assembled (numbered 1-8). If, for example, there was an excess of molecule number 4, the majority of assembled molecules would be 1-4 and 4-8. Assuming only a few hundred bases is being chewed back in the reaction, there would be no sequence homology between the distal region of 1-4 and the proximal region of 4-8, thereby decreasing the amount of 1-8.

Region of Sequence Homology

The region of sequence identity should be sufficiently long to allow specific recombination to occur. That is, it should be long enough so that the region of overlap at the ends of two DNA molecules to be joined is unique to those DNA molecules, and no other DNA molecules will anneal to those two DNA molecules during the recombination reaction. The length can vary from a minimum of about 10 base pairs (bp) to about 300 bp or more. In general, it is preferable that the length of the overlap is less than or equal to about the size of the fragment to be combined, but not less than about 10 bp and not more that about 1000 bp. For the joining of 2 or 3 fragments, about 20-30 bp overlap may be sufficient. For more than 10 fragments, a preferred overlap is about 80 bp to about 300 bp. In one embodiment, the region of sequence identity is of a length that allows it to be generated readily by synthetic methods, e.g., about 40 bp (e.g., about 32 to about 48 bp). The overlaps may be, e.g., about 10, 20, 30, 40, 50, 60, 70, 80, 90, 100, 150, 200, 250, 300, 350, 400, 450, 500, 550, 600, 650, 700, 750, 800, 850, 900, 950 or 1,000 bp in length.

In a preferred embodiment, when a plurality of DNA molecules are to be joined, for each pair of DNA molecules to be joined, the distal region of one of the DNA molecules of the pair is designed to share a region of sequence identity with the proximal region of the other DNA molecule of the pair, and the distal and proximal regions of sequence identity for each pair of DNA molecules are designed to be unique (to be different from the regions of sequence identity of the other pairs of DNA molecules). When the overlapping regions of identity are designed in this manner, the orientation and order of the DNA molecules in the joined molecule can be predetermined. A number of DNA molecules (for example, 4 or 6 molecules) can thus be incubated together in a single reaction mixture (in a single vessel or container) in a method of the invention, and be joined into a longer DNA molecule in which the individual DNAs are arranged in any desired order and orientation.

The regions of sequence identity present in the proximal and distal regions of the DNAs to be joined can be generated by any of a variety of methods.

For example, in one embodiment of the invention, synthetically prepared, overlapping fragments of a gene or genome of interest (e.g., about 5-6 kb in length, or longer or shorter) are optionally amplified (e.g., by PCR, or by MDA such as a rolling circle mechanism) and are joined by a method of the invention in the order and orientation in which they are located in the gene or genome. In this method, the first DNA fragment (e.g., in the 5' most portion of the gene or genome) is synthesized so that the region at its 3' end (the distal end) contains a sequence (e.g., about 40 bp) that is identical to the sequence at the 5' end (the proximal end) of the DNA fragment to which it is to be joined. The second DNA fragment, in turn, is synthesized so that it has, at its distal end, a sequence which is identical to the sequence at the proximal end of the third DNA fragment, and so on. In another embodiment, synthetically prepared fragments of a gene or genome of interest are inserted into a vector, propagated in E. coli to make more of the synthetically prepared fragment, then released from the vector, optionally amplified further by PCR, MDA or RCA, and joined by a method of the invention in the order and orientation in which they are located in the gene or genome. These procedures allow the preparation of a synthetic gene or genome.

In another embodiment of the invention, two fragments to be joined are generated by restriction enzyme digestion, such that the fragments overlap one another, e.g., by about 20 to about 1,000 bp. The overlapping regions can then be joined by a method of the invention. Greater numbers of fragments can also be generated by these methods and joined. Combinations of the preceding method and methods using synthetically prepared DNA molecules and/or molecules generated by PCR can be used.

In one embodiment of the invention, chemically synthesized oligonucleotides, from about 20 bp to any size that can be synthesized chemically, can be used. For example, 10 ssDNA oligonucleotides of about 60 bp, having about 10-20 bp homology overlap at each end, can be assembled simultaneously into a vector. The assembly of 10 such oligonucleotides results in a dsDNA molecule of about 500 bp. DNA molecules assembled by this method can, in turn, be joined to one or more other DNA molecules assembled by this (or another) method (for example, assemblies of about 500 bp). Repetitions of the method can generate very large molecules of DNA; there is no theoretical limit to the size of a DNA molecule thus generated.

In embodiments of the invention, the regions of identity are introduced by PCR amplification.

In one such method, a fragment of interest is inserted into a vector. For example, a plasmid vector can be linearized with a restriction enzyme, generating a sequence A (e.g., having 40 bp) to the left of the restriction enzyme cut and a sequence B (e.g., having 40 bp) to the right of the restriction enzyme cut. The fragment to be cloned into the vector is PCR amplified, using PCR primers which will introduce sequence A at the left end of the fragment, and sequence B at the right end of the fragment. The regions of sequence identity (in this example, each having 40 bp) allow the fragment to be joined to the vector in a desired orientation, to form a circular molecule. Alternatively, particularly when it is desirable to avoid errors which might be introduced into an insert during PCR amplification, the vector can be PCR amplified in order to introduce at the ends of a cloning site sequences which overlap sequences at the ends of the insert. The methods described above allow for the directional cloning of any insert of interest, without having to rely on the presence of, or introduction of, restriction enzyme sites on the insert.

In a variation of the preceding method, two or more DNA fragments are joined to one another to form a linear molecule. In this variation of the preceding method, regions of sequence identity that are unique to each pair of fragments to be joined are introduced into the fragments by PCR amplification, using suitable primers. For each DNA fragment to be joined to another fragment, a sequence is introduced to the 3' (distal) end of the first fragment which overlaps with the sequence at the 5' (proximal) end of the fragment to which it is to be joined. As in the preceding method, PCR primers are used in which the regions of sequence identity (e.g., 40 nt) lie 5' to a PCR primer (e.g., having 20 nt). After a suitable number of rounds of PCR amplification, DNA fragments are produced in which defined regions of sequence identity are present at the ends of the fragments. The resulting fragments can then be joined in a predetermined order and orientation by a method of the invention.

If desired, the joined, linear DNA fragments may be circularized, or they may be inserted into a vector to form a circle (simultaneously with the joining of the fragments, or subsequent to that joining). For example, a vector can be present in the joining reaction, so that the joined fragments are introduced into the vector. The efficiency of joining a large number of fragments (e.g., 6 or 8 fragments) into a vector by a method of the invention is greater than when using a method which employs compatible restriction enzyme sites. In a typical cloning experiment with restriction enzymes and T4 DNA ligase, probability is not in favor of the researcher getting multiple inserts to ligate into a vector. However, in the assembly methods of the invention, a researcher can join about 6 inserts into a vector with approximately 20-50% efficiency, or greater. Furthermore, since the efficiency is high, there is an increased ratio of recombinants to non-recombinants. The background level of non-recombinants can be reduced further by isolating a pure band by agarose gel electrophoresis (since this method produces a high enough yield to isolate a band on agarose gels) or with a sizing column. A DNA of the desired size (having the correct number of joined DNA molecules) can be isolated and introduced into a vector, e.g., using a method of the invention. If the final product is a circle, there is no need to isolate it by agarose gel electrophoresis. Rather, the sample can be treated with an enzyme such as Plasmid-Safe™ (Epicentre), an ATP-dependent DNAse that selectively hydrolyzes linear dsDNA but not circular dsDNA. If the user's application does not require a pure clone, there may be a sufficient amount of DNA without the need to transform into E. coli and do plasmid preparations.

In one embodiment, joined DNA molecules and/or DNA molecules inserted into vectors are introduced into a host cell, such as a bacterial or eukaryotic cell (e.g., by transformation or transfection). Alternatively, the reaction mixture comprising the joined DNA molecules can be introduced into a host cell; only those DNAs which have recombined to form circular molecules can survive in the host cell. In another embodiment, the joined fragments and/or fragments inserted into vectors are used directly, without further passage through a cell, such as a bacterial cell.

Molecular biology methods of the invention can be carried out using conventional procedures. A variety of uses for the inventive method will be evident to the skilled worker. The inventive method can be substituted for any method in which restriction enzyme digests are used to generate compatible sequences for joining DNA molecules. In one embodiment of the invention, DNA molecules that are too large to be amplified by PCR can be cloned by joining sub-fragments by a method of the invention and then inserting them into a suitable vector. Some pieces of DNA are unstable (and therefore, unclonable) in *E. coli*, especially those that are high in A+T % content. A method of the invention allows for the assembly of DNA in vitro without the need to be transformed into *E. coli*. Furthermore, phi29 DNA polymerase can be added to the reaction to amplify the circular DNA. An in vitro recombination system of the invention can be used to recombine any homologous DNAs of interest, e.g., to repair double-stranded DNA breaks or gaps, etc. Another application of the method is to introduce a mutation into a DNA. In this method, a mutation is introduced into both the upper and lower strand PCR primers, so the amplified fragments are 100% mutant; then the fragments are joined by the method of the invention.

One embodiment of the invention is to join cassettes, such as the 5-6 kb DNA molecules representing adjacent regions of a gene or genome of interest, to create combinatorial assemblies. For example, it may be of interest to modify a bacterial genome, such as a putative minimal genome or a minimal genome, so that one or more of the genes is eliminated or mutated, and/or one or more additional genes is added. Such modifications can be carried out by dividing the genome into suitable cassettes, e.g., of about 5-6 kb, and assembling a modified genome by substituting a cassette containing the desired modification for the original cassette. Furthermore, if it is desirable to introduce a variety of changes simultaneously (e.g., a variety of modifications of a gene of interest, the addition of a variety of alternative genes, the elimination of one or more genes, etc.), one can assemble a large number of genomes simultaneously, using a variety of cassettes corresponding to the various modifications, in combinatorial assemblies. After the large number of modified sequences is assembled, preferably in a high throughput manner, the properties of each of the modified genomes can be tested to determine which modifications confer desirable properties on the genome (or an organism comprising the genome). This "mix and match" procedure produces a variety of test genomes or organisms whose properties can be compared. The entire procedure can be repeated as desired in a recursive fashion.

The disclosed methods can be used to join any nucleic acid molecules of interest. The nucleic acid molecules can come from any source, including a cellular or tissue nucleic acid sample, cloned fragments or subclones thereof, chemically synthesized nucleic acids, genomic nucleic acid samples, cDNAs, nucleic acid molecules obtained from nucleic acid libraries, etc. The DNAs can be radioactively labeled or can comprise binding entities, such as biotinylated nucleotides, which can aid in the purification of the joined DNAs. If desired, the DNA molecules to be joined, or primers for adding overlapping regions of sequence identity, can be prepared synthetically. Conventional synthesis techniques include using phosphoroamidite solid-phase chemistry to join nucleotides by phosphodiester linkages. Chemistry for joining nucleotides by phosphorothioate linkages or different linkages, such as methylphosphonate linkages, can also be used. For example, the cyanoethyl phosphoramidite method can be used, employing a Milligen or Beckman System 1 Plus DNA synthesizer (for example, Model 8700 automated synthesizer of Milligen-Biosearch, Burlington, MA or ABI Model 380B). Synthetic methods useful for making DNA molecules are also described by Ikuta, et al., *Ann Rev. Biochem*. (1984) 53:323-356, (phosphotriester and phosphite-triester methods), and Narang, et al., *Methods Enzymol*. (1980) 65:610-620 (phosphotriester method). DNAs prepared by methods as above are available from commercial sources, such as Integrated DNA Technologies (IDT), Coralville, IA.

Methods of the invention are amenable to automation and to adaptation to high throughput methods, allowing for the joining of multiple DNA molecules simultaneously by computer-mediated and/or robotic methods that do not require human intervention.

DNA Modifications and Nucleotide Analogs

DNA used in a method of the invention can be modified in any of a variety of ways, provided that the modified DNA is able to function in the method. A skilled worker can readily determine if a particular modification allows the modified DNA to function (e.g., to be recognized by and acted upon by enzymes used in the method).

DNAs used in methods of the invention can have one or more modified nucleotides. For example, they may contain one or more modifications to either the base, sugar, or phosphate moieties. Modifications to the base moiety would include natural and synthetic modifications of A, C, G, and T as well as different purine or pyrimidine bases, such as uracil-5-yl, hypoxanthin-9-yl (I), and 2-aminoadenin-9-yl. Base modifications often can be combined with for example a sugar modification, such as 2'-O-methoxyethyl, to achieve unique properties such as increased duplex stability.

Nucleotide analogs can also include modifications of the sugar moiety. Modifications to the sugar moiety would include natural modifications of the ribose and deoxyribose as well as synthetic modifications. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar.

Nucleotide analogs can also be modified at the phosphate moiety. It is understood that these phosphate or modified phosphate linkages between two nucleotides can be through a 3'-5' linkage or a 2'-5' linkage, and the linkage can contain inverted polarity such as 3-5' to 5'-3' or 2'-5' to 5-2'. Various salts, mixed salts and free acid forms are also included. It is understood that nucleotide analogs need only contain a single modification, but may also contain multiple modifications within one of the moieties or between different moieties.

Nucleotide substitutes are nucleotides or nucleotide analogs that have had the phosphate moiety and/or sugar moieties replaced. Nucleotide substitutes include molecules having similar functional properties to nucleotides, but which do not contain a phosphate moiety, such as peptide nucleic acid (PNA). Nucleotide substitutes include molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. It is also understood in a nucleotide substitute that both the sugar and the phosphate moieties of the nucleotide can be replaced, by for example an amide type linkage (aminoethylglycine) (PNA).

DNA molecules of the invention can be made up of different types of nucleotides or the same type of nucleotides. The nucleotides can be comprised of bases (that is, the base portion of the nucleotide) and can comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

One-Step Isothermal Method

One aspect of the invention is an in vitro method, using isolated (e.g., substantially purified) proteins, for joining two or more double-stranded (ds) or single-stranded (ss) DNA molecules of interest, wherein the distal region of the first DNA molecule and the proximal region of the second DNA molecule of each pair share a region of sequence identity, comprising incubating the at least two DNA molecules in a single vessel, at about 45-60° C., with (a) a non-thermostable, 5' (51 to 3') exonuclease (e.g., T5 or lambda exonuclease, and/or wherein the exonuclease is not T7 exonuclease), (b) a crowding agent (e.g., PEG, such as about 5% PEG, e.g., PEG-8000), (c) a thermostable non-strand-displacing DNA polymerase which exhibits a 3' exonuclease activity (e.g., a polymerase that intrinsically exhibits a 3' exonuclease (proofreading) activity, such as PHUSION® or VENT$_R$® DNA polymerase; or a mixture of a polymerase, such as Taq polymerase, which lacks a proofreading activity, and a titered amount (usually a small amount) of an enzyme such as PHUSION® or VENT$_R$® polymerase, which has a 3' exonuclease activity), and (d) a thermostable ligase (e.g., Taq ligase), under conditions that are effective for joining the at least two DNA molecules to form a substantially intact dsDNA molecule (e.g., in which a single copy of the region of sequence identity is retained, and/or in which unpaired, non-homologous, single-stranded DNAs are digested and removed.

In the preferred isothermal method, the polymerase of (c) comprises a 3' exonuclease activity. This enzymatic activity can be an intrinsic property of the polymerase (c); for example, PHUSION® and VENT$_R$® DNA polymerases are thermostable, non-strand-displacing, DNA polymerases which exhibit a proofreading activity (a 3' exonuclease activity). Alternatively, polymerase (c) can be a combination of an enzyme such as Taq polymerase, which lacks a proofreading activity, with a titrated amount (usually a small amount) of a thermostable polymerase such as PHUSION® or VENT$_R$® polymerase, which has a 3' exonuclease activity. This 3' exonuclease activity is useful, for example, when it is desirable to add sequences such as primer binding sites to the ends of the DNA molecules to be joined, e.g., in order to allow PCR amplification of the molecules by universal primers, but then to remove the primer binding sites during the assembly procedure. The ability to use universal primers to amplify DNA molecules to be joined, and then to be able to remove during the assembly reaction the binding domains in the molecules which allow the universal primers to be used, is an advantage of the invention.

An advantage of this method of the invention is that one can join DNA molecules which initially lack 5' phosphorylated ends (e.g., DNAs prepared by PCR amplification), even though a 5' phosphorylated end is required for ligase to join a 5' end to a 3' OH group. This is because the 5' exonuclease, as it removes nucleotides from the 5' end of a substrate DNA, leaves 5' phosphorylated ends.

Without wishing to be bound by any particular theory, it is suggested that, when the mixture of components is incubated at an elevated temperature (about 45-60° C., e.g., at about 50° C.), the DNA polymerase is able to "win" the competition with the exonuclease activity, so that the gaps formed by digestion with the exonuclease are filled in by the polymerase substantially immediately after they are formed. This is achieved because the exonuclease is not thermostable, and thus is weakly active at the elevated temperature and is inactivated after about 10-15 minutes of incubation, whereas the polymerase functions well at the high temperature, driving the reaction to fill in the gaps; the nicked molecules thus formed can then be ligated by the thermostable ligase. By a "thermostable" enzyme is meant an enzyme that can function well at a temperature of at least about 45° C.-60° C.

Because the buffer conditions for assembling DNA molecules by a method of the invention are also suitable for PCR amplification, and an assembly mixture already contains PHUSION® polymerase, PCR can be performed following an assembly reaction without changing the buffer conditions. In one embodiment, once assembly is completed, the vessel holding the reaction components is opened and primers for PCR are added. In another embodiment, the primers are already contained within the assembly mixture from the start of the reaction. In this embodiment, following assembly, the vessel does not have to be opened, and the PCR reaction can begin immediately and proceed by the standard procedure. When primers are contained within the assembly mixture, it may be necessary to add the primers in excess (e.g., ~5,000 nM) of normal primer concentrations in PCR (usually 500 nM), to prevent degradation of some or most of the PCR primers by the exonuclease during the assembly step.

Kits for in vitro joining two or more double-stranded (ds) or single-stranded (ss) DNA by the preferred isothermal method, comprise, in a single container, (a) a non-thermostable, 5' exonuclease (e.g., wherein the exo is T5 or lambda exonuclease; wherein the exo is T5; wherein the exo is not T7 exonuclease), (b) a crowding agent (e.g., PEG, such as about 5% PEG-8000), (c) a thermostable non-strand-displacing DNA polymerase which exhibits a 3' exonuclease activity (e.g., a polymerase that intrinsically exhibits a 3' exonuclease (proofreading) activity, such as PHUSION® and VENT$_R$® DNA polymerase; or a mixture of a polymerase, such as Taq polymerase, which lacks a proofreading activity, and a titered amount (usually a small amount) of an enzyme such as PHUSION® or VENT$_R$® polymerase, which has a 3' exonuclease activity), and (d) a thermostable ligase (e.g., Taq ligase), in suitable amounts such that, when dsDNA molecules or ssDNA oligonucleotides are added to the kit in the presence of a suitable buffer composition and dNTPs and incubated for about 15-60 minutes, at about 45° C. to about 60° C., the DNA molecules are assembled, in a concerted reaction.

In one embodiment, the kit comprises the components of the Oligonucleotide Assembly Mixture shown in Example III A. A kit of the invention may be stored frozen, e.g., at about −20° C.

Any of a variety of 5' to 3', double-strand specific exodeoxyribonucleases may be used to chew-back the ends of DNA molecules in the methods of the invention. The term "5' exonuclease" is sometimes used herein to refer to a 5' to 3' exodeoxyribonuclease. A "non-processive" exonuclease, as used herein, is an exonuclease that degrades a limited number of (e.g., only a few) nucleotides during each DNA binding event. Digestion with a 5' exonuclease produces 3' single-stranded overhangs in the DNA molecules. Among other properties which are desirable for a 5' exonuclease are that it lacks 3' exonuclease activity, it generates 5' phosphate ends, and it initiates degradation from both 5'-phosphorylated and unphosphorylated ends. It also desirable that the enzyme can initiate digestion from the 5' end of a molecule, whether it is a blunt end, or it has a small 5' or 3' recessed end. Suitable exonucleases will be evident to the skilled worker. These include, e.g., phage T5 exonuclease (phage T5 gene D15 product), phage lambda exonuclease, RecE of Rac prophage, exonuclease VIII from $E.\ coli$, phage T7 exonuclease (phage T7 gene 6 product), or any of a variety of 5' exonuclease that are involved in homologous recombination reactions. In one embodiment of the invention, the exonuclease is T5 exonuclease or lambda exonuclease. In another embodiment, the exonuclease is T5 exonuclease. In another embodiment, the exonuclease is not phage T7 exonuclease. Methods for preparing and using exonucleases and other enzymes employed in methods of the invention are conventional; and many are available from commercial sources, such as USB Corporation, 26111 Miles Road, Cleveland, Ohio 44128, or New England Biolabs, Inc. (NEB), 240 County Road, Ipswich, MA 01938-2723.

When a 5' exonuclease is used, single-stranded overhangs are generated at the 5' end of DNA molecules which cannot be repaired, unless, e.g., the molecules can form a circle, or other procedures are introduced to block exonuclease digestion of these 5' termini. Non-strand-displacing DNA polymerases used in methods of the invention must elongate in the 5' direction from a primer molecule. Because no primer is available to be extended in the 5'-located gap in a DNA molecule which has been chewed back with a 5' exonuclease, the gap cannot be filled in by a polymerase. In one embodiment of the invention, the DNA molecules to be joined are selected (designed) so that the two terminal DNA molecules join to one another to form a circle. In another embodiment, the joined DNA molecules are designed so that they become integrated into a vector which is also present in the reaction mixture. Alternatively, in one embodiment of the invention, the 5' ends of the terminal DNA molecules that are to be joined are blocked so that 5' exonuclease cannot digest them. The blocking agent is preferably reversible, so that the joined DNA molecule can eventually be joined into a vector. Suitable blocking agents will be evident to the skilled worker. These include, e.g., phosphorothioate bonds, 5' spacer molecules, locked nucleic acid (LNA), etc.

As is discussed elsewhere herein with regard to the removal of non-homologous sequences, it is desirable that a thermostable, non-strand-displacing, DNA polymerase to be used in a method of the invention exhibits a 3' exonuclease (proofreading) activity. Among suitable DNA polymerases having such a 3' exonuclease activity are PHUSION® polymerase, VENT$_R$® polymerase or DEEP VENT$_R$™ polymerase (which have strand-displacing activity when used at 55° C. or lower), Pfu polymerase and 9° N$_m$™ polymerase. Alternatively, one can use a thermostable, non-strand-displacing, DNA polymerase which lacks a 3' exonuclease activity, if one also includes a small amount of a second enzyme which can provide the 3' exonuclease activity. For example, one can use Taq polymerase, plus a small amount of one of the polymerases noted above that have 3' exonuclease activity. A skilled worker can readily titrate how much of the second enzyme to include, in order to achieve the desired amount of exonuclease activity.

In many of the examples used herein, PHUSION® polymerase is used. This polymerase is desirable because, among other properties, it exhibits a high degree of fidelity.

A kit for conducting this method can comprise (a) an isolated (e.g., substantially purified) enzyme having a non-thermostable, 5' exonuclease activity (e.g., T5 exonuclease or lambda exonuclease, but preferably not T7 exonuclease); (b) a crowding agent, such as PEG (e.g., about 5% final concentration of PEG-8000); (c)(i) an isolated thermostable, non-strand-displacing DNA polymerase which exhibits a proofreading 3' exonuclease activity (e.g., PHUSION® or VENT$_R$® polymerase); or (c)(ii) an isolated thermostable, non-strand-displacing DNA polymerase which does not exhibit a proofreading 3' exonuclease activity (e.g., Taq polymerase), in combination with a suitably small amount of a polymerase having a 3' exonuclease activity (e.g., PHUSION® or VENT$_R$® polymerase); and (d) an isolated, thermostable ligase (e.g., Taq DNA ligase). Other components of a kit of the invention can include a suitable buffer solution, which comprises a buffer at pH about 7.5 (such as Tris), a suitable amount of $MgCl_2$, the four dNTPs, an energy source (such as ATP or NAD), and, optionally, a suitable cloning (assembly) vector, such as a pUC vector. These components can be packaged in amounts suitable for a single use, in individual vessels, to which DNA molecules to be joined are added; or the components can be present in a larger volume, which can be distributed in aliquots suitable for individual joining reactions.

An exemplary kit contains an optimized 1.33× mixture of Tris pH 7.5, MgGh, the four dNTPs, DTT, PEG-8000, NAD, T5 exonuclease, PHUSION® polymerase, Taq ligase and, optionally, an assembly vector. A kit of the invention is generally packaged in a containers in which the components are stable, e.g., it can be stored frozen, at about −20° C.

In one embodiment of the invention, 5 μL of a pool of dsDNA or ssDNA molecules (e.g., oligonucleotides, such as 60-mers that overlap each other by 20 bases) to be assembled are combined with 15 μL of the mixture of the kit, to generate a total of 20 μL. This mixture is then incubated at about 45-60° C. (e.g., at about 50° C.) for about 15-60 minutes (e.g., 15, 30, 45 or 60 minutes), during which time the DNA molecules assemble into a contiguous segment of dsDNA. If desired, a kit can further contain an assembly vector (e.g., a cloning vector), such as pUC 19, pBR322 or a BAC.

Optionally, kits of the invention comprise instructions for performing the method, e.g., instructions for designing oligonucleotides to be assembled, and/or directions for diluting a pool of oligonucleotides to a suitable concentration. For example, the inventors have found that about 180 fmol/μL of each oligonucleotide in 5 μL is optimal for assembling eight 60-mers with 20 base overlaps. Other optional components of a kit of the invention include a positive control; for the example noted above, a control can contain eight 60-mers with 20 base overlaps that have been demonstrated to assemble by a method of the invention, as well as a vector, such as pUC19. A kit can also contain, if cloning of the assembled DNAs is desired, instructions for transforming the assembled mixture into a suitable microorganism, such as $E.\ coli$, and selecting for transformants on an agar plate containing growth medium (e.g., LB) and a suitable selective marker (e.g., for pUC19, carbenicillin or ampicillin). A kit can also comprise instructions concerning suitable strains for transformation, parameters for electroporation, etc.

One-Step Thermocycled Method

Another aspect provides a method comprising incubating the ds DNA or ss DNA molecules with
- (a) a non-thermostable, 3' exonuclease operable in the presence of dNTPs, which "chews-back" the ends of the double-stranded DNA molecules, to expose single-stranded overhangs comprising the regions of overlap;
- (b) a crowding agent;
- (c) a thermostable non-strand-displacing DNA polymerase conjugated to a moiety in a temperature-sensitive manner to block the polymerase activity below the activity temperature;
- (d) a thermostable ligase, which seals (ligates) the nicks thus formed;
- (e) dNTPs; and
- (f) a suitable buffer.

The exonuclease of (a) is rendered inactive at a high temperature (e.g., 75° C.). The exonuclease is active at a lower temperature, e.g., 37° C.

The polymerase of (b) may exhibit an activity temperature between 37° C. and 75° C. and the polymerase may be active above this temperature. Without wishing to be bound by a particular mechanism, the inactivating moiety remains conjugated to the polymerase below the activity temperature. At the activity temperature, the antibody becomes unbound and the polymerase exhibits activity. For example, at 75° C., the antibody is unbound from the polymerase and the polymerase is active.

Preferably, the ligase of (c) is thermostable at 75° C. or higher. The ligase need not be active at 75° C. or higher, but if active at a lower temperature, the activity must be present when the temperature is lowered from 75° C. or higher to the lower temperature (e.g., 60° C.).

In the method of the invention, when the mixture of components is first incubated at a low temperature (about 30-45° C., e.g., at about 37° C.), the exonuclease is active and forms gaps on the DNA, while the DNA polymerase is inactive due to steric interference on the part of the bound inhibiting moiety such as an antibody or biotin. When the temperature is raised to a high temperature (above 65° C., e.g., at about 75° C.), the exonuclease is rendered inactive and the DNA polymerase is rendered active as the antibody dissociates from the polymerase. When the temperature is lowered to about 60° C., the ligase is active to fill in the gaps.

The entire procedure is carried out as a "one-step" reaction (in a single tube, which does not have to be opened during the entire recombination procedure, in a thermocycler apparatus). In one such procedure, a mixture of the DNAs to be joined is incubated at 37° C. with exonuclease III; Taq DNA polymerase which is rendered inactive through conjugation to an antibody; Taq DNA ligase; dNTPs and a buffer compatible with all of these enzymatic activities. The temperature is then raised to 75° C. At this temperature, exonuclease III is inactivated, the chewed back DNAs begin to anneal, and the antibody begins to dissociate from Taq DNA Polymerase, resulting in activation. The temperature is then decreased to 60° C. to complete the repair reaction (filling in the gaps and sealing the nicks).

An advantage of a method of the invention is that the particular method allows exonuclease activity in the presence of dNTPs. Without wishing to be bound by a particular mechanism, use of exonuclease III permits exonuclease activity in the presence of dNTPs, while the exonuclease activity of T4 DNA polymerase is blocked by dNTPs. Thus, when using exonuclease III there is no need to stop the reaction and add dNTPs in a separate step.

Another advantage of a method of the invention is that all of the steps may be performed in vitro, as a complete recombination system. Other systems known in the art require transformation into a host cell in order to repair the nucleotide fragments produced. The current system encompasses a repair step in vitro using the ligase such that the transformation into a host cell is avoided. This is particularly useful if the nucleotide to be repaired would be toxic to a host cell and thus not able to undergo transformation.

Yet another advantage of a method of the invention is that the 5' and 3' overhangs are repaired in the nucleotide produced. Other isothermal one-step methods do not involve repairing the 5' and 3' overhangs.

Another aspect of the invention is a kit for the in vitro joining of two or more double-stranded (ds) DNA molecules of interest, wherein the distal region of the first DNA molecule and the proximal region of the second DNA molecule of each pair share a unique region of sequence identity, comprising, in a single container,
- (a) a non-thermostable, 3' (3' to 5') exonuclease operable in the presence of dNTPs,
- (b) a crowding agent,
- (c) a thermostable non-strand-displacing DNA polymerase conjugated to a chemical moiety in a temperature sensitive manner to block the polymerase activity below the activity temperature, and
- (d) a thermostable ligase, and optionally
- (e) dNTPs, and
- (f) a suitable buffer, in suitable amounts such that, when dsDNA molecules or ssDNA oligonucleotides and when needed, dNTPs, a crowding agent, and as suitable buffer, are added to the contents of the mixture and incubated for about two to ten minutes, at 37° C., then 10-40 minutes at 75° C., and then for 30 minutes to two hours at 60° C., the DNA molecules are assembled. A kit of the invention may be stored frozen, e.g., at about –20° C.

In an embodiment of this aspect, in step (c) the incubation steps may be five minutes at 37° C., then 20 minutes at 75° C., and then for one hour at 60° C.

Any of a variety of 3'→5', double-strand specific exodeoxyribonucleases may be used to chew-back the ends of DNA molecules in the methods of the invention. The term "3' exonuclease" refers to a 3'→5' exodeoxyribonuclease. Suitable exonucleases will be evident to the skilled worker. These include, e.g., exonuclease III. In one embodiment of the invention, the exonuclease is exonuclease III. Methods for preparing and using exonucleases and other enzymes employed in methods of the invention are conventional; and many are available from commercial sources, such as USB Corporation, 26111 Miles Road, Cleveland, Ohio 44128, or New England Biolabs, Inc. (NEB), 240 County Road, Ipswich, MA 01938-2723.

Preferably in the one-step thermocycled method, the 3' exonuclease is not active as a polymerase.

Combinatorial Methods for Optimization

In preferred embodiments, the isothermal methods of the present invention can be used to modify the properties of a whole nucleic acid molecule, for example, to optimize the expression, function, activity, yield, etc., of a polypeptide encoded by the nucleic acid molecule. The combinatorial methods described herein provide a multitude of possible nucleic acid sequences that can be screened for the desired outcome. In alternative embodiments, the nucleic acids could provide other DNA or RNA products, for example, antisense RNA that is used to decrease the yield of another product in a host cell. The outcome of the combinatorial approach is to provide a desired product that is not found in nature, or is an improvement or optimization of a natural product. Optimized products may be synthetic components, natural components that have been modified or rearranged, or combinations of natural and synthetic components. One of skill in the art could envision multiple additional applications of the combinatorial methods described herein.

Whatever the level at which recombination occurs, the intermediate product is a mixture of nucleic acids encoding proteins that typically are expressed and tested for yield and, in the embodiments other than codon optimization, activity. Thus, typically the mixture of nucleic acids is provided with restriction sites or overlapping portions that permit insertion of the nucleic acids into expression systems that contain control sequences, notably promoters and termination signals. The choice of control sequences, depends, of course, on the host in which expression is to take place. The optimal control sequences for any particular intended host can also be determined by constructing appropriate libraries containing a multiplicity of control sequences such as promoters, enhancers and termination sequences and assembled in a multiplicity of genes wherein the most favorable assembly of control sequences can be identified. Convenient hosts include *E. coli*, other bacterial systems and yeast as well as other unicellular fungi. Mammalian host cells or insect host cells could also be used as could plant cells. The choice of the host for testing is a matter of experimental preference and expression controls for all of these hosts are well known.

Once the mixture has been treated to insert the coding sequences into expression systems, it is used to transfect the appropriate cells which are then diluted and cultured. Depending on the desired end point, the protein activity, yield or metabolic activity of the cultures is assessed for the culture with the highest value. The nucleic acid is then retrieved from this culture and sequenced or otherwise identified as the desirable sequence or sequences. Depending on the level of optimization—i.e., codon usage, individual protein optimization, metabolic pathway optimization, or gene synthesis, the next combinatorial step can be achieved by assembling optimal components.

Methods of in vitro assembly described above may be used to conduct this process. Additionally, methods of in vivo assembly may be used to conduct this process, as described above. Furthermore, a combination of in vitro and in vivo assembly may be used to conduct this process.

However, as to the various recombination systems, the initial steps of nucleic acid construction differ in their components.

Figure 7A:
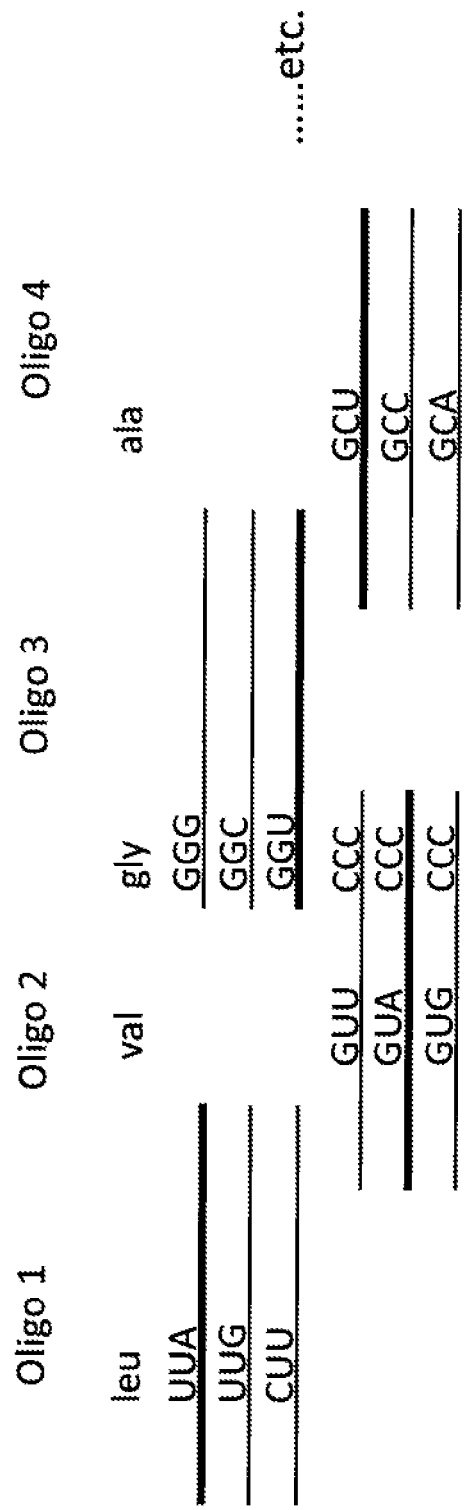
FIG. 7A is a schematic illustrating the use of codon optimization to create a combinatorial library of assembled fragments.

For codon optimization, as shown in FIG. 7A, a coding sequence is constructed as shown therein by varying the codons in each nucleic acid used to assemble the coding sequence. As shown in FIG. 7A, a protein that includes leucine, valine, glycine and alanine is assembled from individual fragments where the codons for these individual amino acids is varied. By suitable overlap segments, a mixture containing all of the nucleotides shown in FIG. 7A can be assembled in the correct order in a single reaction mixture as described above. The resultant will be full-length coding sequences. If desired, an expression vector may also be added to the mixture to provide the control sequences automatically at this stage. The assembled coding sequences provided further with expression controls, if necessary, are then transfected into host cells, and cultured individually and the level of protein assessed using standard protein determination techniques. The colonies with the highest levels of protein production are analyzed by extracting the expression system and sequencing to identify the optimal set of codons.

In general, while highest levels of production or activity are referred to, it is understood that it is not necessary to select the exact highest value in each case. For various reasons, it may be sufficient simply to select for satisfactory levels of these characteristics.

In more detail, a method to identify a nucleotide sequence that optimizes codon usages for production of a protein comprises at least the following steps (a) through (e). In step (a), oligomers are provided encoding portions of the protein containing degenerate forms of the codon for an amino acid encoded in the portions, with the oligomers extended to provide flanking coding sequences with overlapping sequences. In step (b), the oligomers are treated to effect assembly of the coding sequence for the protein. The reassembled protein is included in an expression system that is operably linked to control sequences to effect its expression. In step (c), the expression system is transfected into a culture of compatible host cells. In step (d), the colonies obtained from the transformed host cells are tested for levels of production of the protein. In step (e), at least one colony with the highest or a satisfactory production of the protein is obtained from the expression system. The sequence of the portion of the expression system that encodes the protein is determined.

For an embodiment wherein control sequences are to be optimized, one or more coding sequences are used in the construction of a library containing a multiplicity of expression systems. The components to be assembled into the expression systems include a variety of promoters, enhancers, termination sequences and the like, the selection of which will depend on the nature of the intended recombinant host. Again, the components are provided with overlapping sequences to assure assembly in the correct order. Using any in vitro assembly technique, a variety of genes with different control sequences is obtained which are then transfected into host cells and cultured individually to determine levels of protein production.

In more detail, to construct a gene with optimal control sequences for expression, the method comprises at least the following steps (a) through (e). In step (a), oligomers representing a multiplicity of promoters, enhancers, and termination sequences and oligomers comprising encoding sequences for a protein are provided. In step (b), oligomers to affect assembly of genes for the protein are treated. In step (c), the resulting genes are transfected into a culture of compatible host cells. In step (d), colonies obtained from the transformed host cells are tested for levels of production of the protein. In step (e), the gene is obtained from at least the colony with the highest or satisfactory level of production of the protein. The sequence of the control sequences associated with the nucleotide sequence encoding the protein is determined.

Figure 7B:
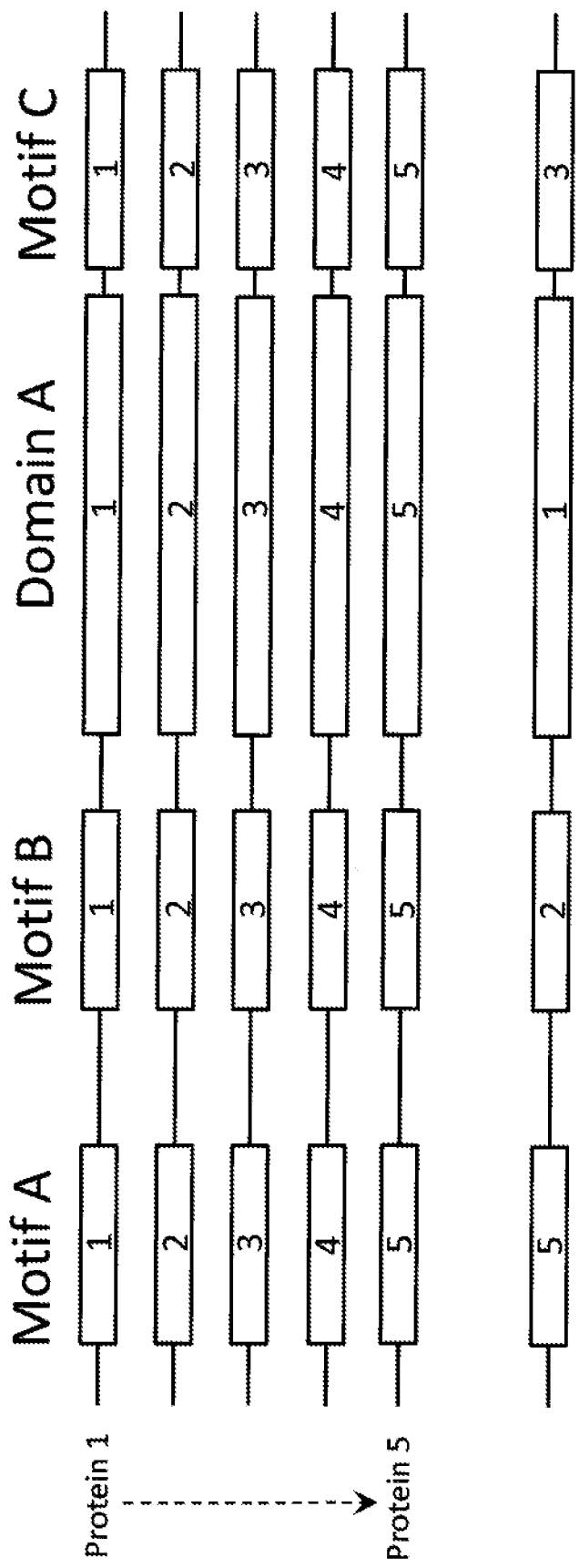
FIG. 7B is a schematic illustrating the use of a multiplicity of motif and domain variants to create a combinatorial library of a gene.

At the next level, illustrated in FIG. 7B, the coding sequences of several variants of a protein of given activity are assessed for motifs and domains. Nucleic acid sequences encoding each of the motifs and domains shown are then individually synthesized and provided suitable overlapping sequences to provide a correct order of assembly. These synthetic sequences are then provided in a ligation mixture similar to that described above with respect to codon optimization, optionally including a vector to provide control sequences, and the resulting expression systems are transfected into host cells and tested for activity and/or yield.

To identify a nucleotide sequence that encodes an optimized form of a protein having a desired activity, the method comprises the following steps (a) through (f). In step (a), domains and motifs contained in a series of variants of the protein are identified. In step (b), oligomers encoding each of the domains and motifs from the variants are provided. In step (c), the mixture is treated to effect assembly into sequences encoding the protein. The assembly is conducted so as to provide the coding sequences with operably linked control sequences for expression, to obtain a mixture of expression systems. In step (d), the expression systems are transformed into a culture of compatible host cells. In step (e), the colonies obtained from the cells are tested for activity of the produced protein. In step (f), the expression system is isolated from at least the colony that produces the protein of highest or satisfactory level of activity. The nucleotide sequence encoding said protein is then identified.

Figure 7C:
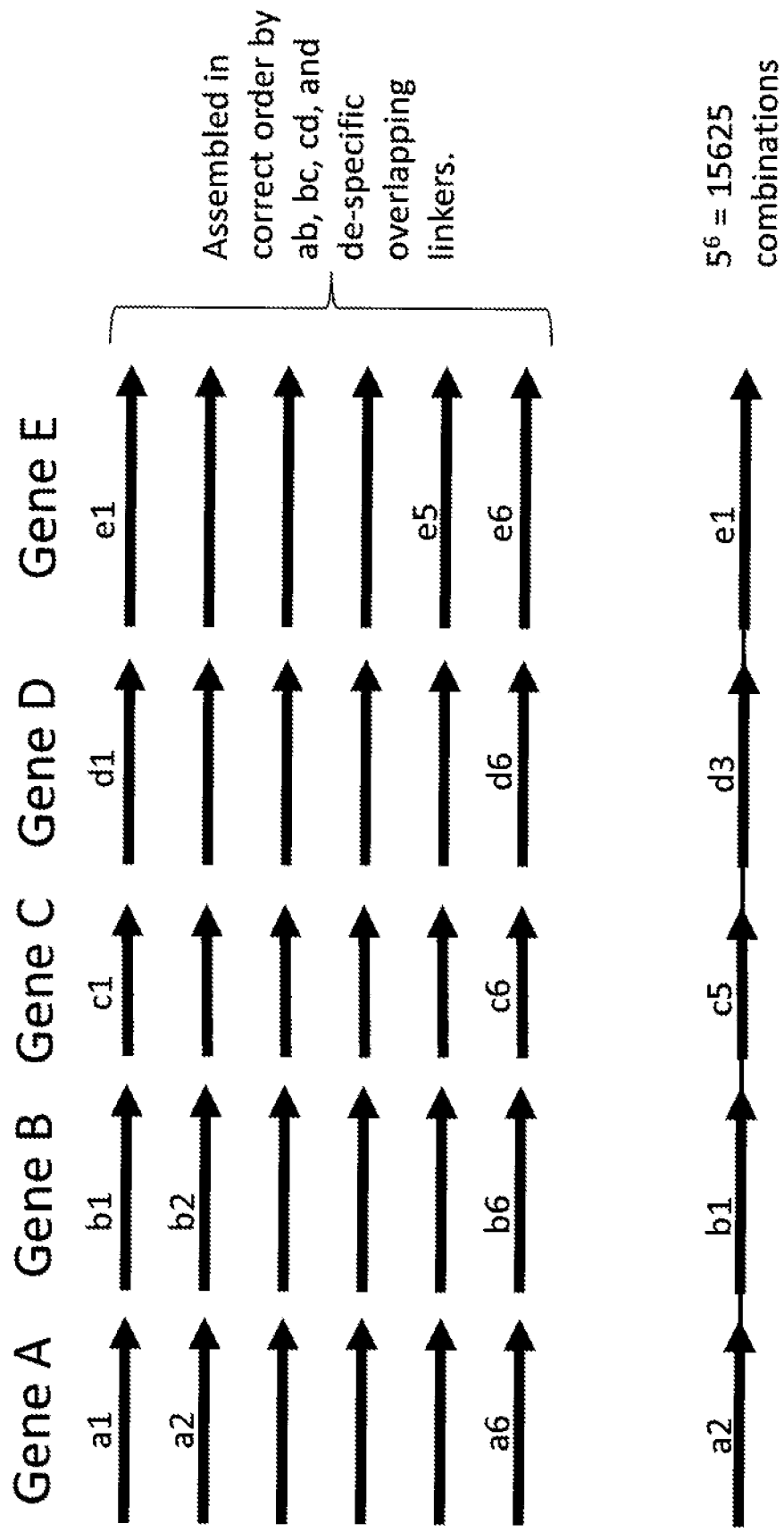
FIG. 7C is a schematic illustrating the use of variant genes to create a combinatorial library of a metabolic pathway.

At the next level, shown in FIG. 7C, variants of proteins that are responsible for a metabolic pathway are individually synthesized, mixed and matched as described above, and tested for the production of metabolic products. The pathways may be assembled on a single vector or multiple vectors may be used in successive transformations. Variants may include upstream promoter elements of the genes encoding the proteins from different species as well as synthetically generated upstream promoter elements.

Finally, in one embodiment, assemblies of the desirable metabolic pathways and/or genes may be combinatorially assembled into complete genomes using a similar approach. As described in Gibson, et al., *Science* (2008) 319:1215-1220, an entire bacterial genome can be assembled by a combination of in vitro and in vivo techniques. Minimal genomes may also be assembled in this way.

In one embodiment, entire pathways may be assembled using appropriate linkers to construct an entire genome. The methods for assembly and testing are similar to those described above. Because assembly of several DNA pieces takes place in a single reaction operating at a single temperature, it is possible to carry out the reaction in a highly parallel fashion to build, in stages, an entire chromosome. The pathway variants may all be cloned into a bacterial artificial chromosome (BAC) vector, or any other vector useful for the manipulation of large nucleic acids.

To optimize metabolic pathways, the method comprises constructing nucleic acid molecules encoding variants of each enzyme in the pathway to be optimized. All of the encoding sequences can be assembled using the technique described above of overlapping sequences on a single vector for each different pathway, or independent vectors for each member of the pathway can be employed by mixing the vectors for each member in successive transformation mixtures. Control sequences to effect expression of the enzymes in the pathway are provided. Colonies derived from the culture are assessed for favorable characteristics conferred by the pathway to be optimized, and the expression systems of successful colonies are sequenced.

The construction of optimal or minimal genomes need not be based solely on a combination of metabolic pathway assemblies. Individual genes may also be assembled in a similar manner or a combination of individual genes and metabolic pathways may be so assembled. To determine the necessity for one or more genes to a metabolic pathway, each of these could be systematically eliminated from the assembly.

In all of the foregoing methods, DNA molecules can be assembled using robotic systems at some or all of the levels described. At any stage, either in vitro or in vivo methods may be used. Assembly of entire genomes may be desirable. Using the techniques described by Gibson, et al., chromosomes of 20-500 kb can be constructed in a combinatorial manner as described above. For assembly of nucleotide sequences that generate complete optimized metabolic pathways the optimal combination of these systems is evaluated.

The processes described above may be conducted ab initio, without preselection of putatively desirable elements or may include selection of appropriate variant genes for each of the pathway genes from sequence databases, from all available sequence libraries including completed genomes and environmental libraries. Computational approaches may be used to select the most likely candidates from the many available choices. Results with one combinatorial library might help to design a second library for the same pathway that would give even better production of the desired product.

Optimum codon usage for expression in the chosen production host cell can also be designed based on computational methods and tested as described above.

As noted above, appropriate regulatory signals are added for the chosen production host, including transcriptional promoters and terminators, and appropriate signals for initiation of protein synthesis, as well as suitable linker sequences specific for each gene-gene junction in the pathway and for joining the assembled pathway to the cloning vector.

Optimal sizes and overlaps of the individual oligonucleotides for the entire assembly, may also be designed. Design tools include a graphical interface to aid in initial pathway design and to view the final sequence design. In the case of combinatorial libraries it should be possible to call up and view any individual chromosome within the library with a single mouse click on each component gene.

As to assembly of a pathway, for illustration, assuming an average gene size of 1200 bp and an average oligonucleotide size of 60 nucleotides, roughly $1200 \times 9 \times 10 \times 2/60 = 3,600$ oligonucleotides are needed for the construction of a 9 gene pathway, excluding control elements which are small relative to genes. The factor of 2 is because the oligonucleotides have to cover both strands of the DNA. Oligonucleotides can be purchased from any of a dozen or so suppliers, or synthesized automatically. The oligonucleotides, which are supplied in 96-well oligonucleotide trays, are robotically distributed into 96-well assembly reaction trays such that each well in the assembly trays would contain 8 adjacent oligonucleotides in the sequence. The number of trays could then be reduced at the first assembly step from approximately 36 oligonucleotide trays down to around 5 assembly trays. A 15 µl aliquot of the thawed assembly reaction mixture (which already includes the cloning vector as a ninth DNA piece) is transferred to each well. The trays are then incubated for 20 minutes at 50° C. The assembly product in each well consists of 8 assembled oligonucleotides inserted into the vector DNA to form a circle. Aliquots of each well are pooled together, cloned and sequenced. Correct clones are transferred back into 5 trays for the next assembly step. By sequencing up front at the first stage of assembly when the assemblies are small, oligonucleotide errors are weeded out, and all subsequent assemblies will generally have correct sequence.

To go from one assembly step to the next, the assemblies are "lifted out" of the vector by high fidelity PCR and aliquots are distributed to the next set of trays for the next assembly reaction.

Assembly continues until a single tray contains 10 variants of each of the 9 genes. The 9 genes and their variants are then pooled into a final assembly reaction that results in a library of 109 different combinations of the 9 gene pathway cloned into the BAC vector. This combinatorial library is transformed into the appropriate host cell, and individual clones are screened for product yield, etc.

The invention thus provides a method of assembling entire genomes by using the optimized components described above. As noted above, the "entire" genome may be a minimal genome, the nature of which is determinable as described in the above-cited PCT publication or may be determined arbitrarily by selecting only certain identified components of the library desired. The library components may be individual genes, assemblies of individual genes according to metabolic pathways, assemblies of genes that are otherwise organized, or a combination of individual genes and organized systems thereof. Desirably, the components are indeed optimized as described herein; however, this is not a prerequisite. Libraries of individual genes and/or assemblies of genes, some or all of which may be optimized with regard to motif variants, control sequences and/or codon usage may be used in the genome assembly.

EXAMPLES

In the following examples, all temperatures are set forth in uncorrected degrees Celsius; and, unless otherwise indicated, all parts and percentages are by weight.

Example I

Thermocycled Exonuclease III One-Step Assembly System Protocol

A thermocycled one-step assembly was developed based on the use of an isolated non-thermo stable 3' to 5' exonuclease and an isolated heat-activated DNA polymerase as follows. A reaction was set up on ice in a 0.2 ml PCR tube containing the following: 100 ng each substrate DNA to be assembled, 20 µl of 4×CBAR buffer, 0.7 µl of exonuclease III (4 U/µl, NEB), 8.0 µl of Taq DNA ligase (40 U/µl, NEB), 0.5 µl of AmpliTaq® Gold (5 U/µl, Applied Biosystems), and water to 80 µl. The 4×CBAR (Chew-back, Anneal, and Repair) Buffer was 20% PEG-8000, 600 mM Tris-Cl, 40 mM MgCl$_2$, 40 mM DTT, 4 mM NAD, and 800 µM each dNTP (pH 7.5).

This gave a final concentration of 1.25 ng/µl of each DNA that was to be assembled, 5% PEG-8000, 150 mM Tris-Cl pH 7.5, 10 mM MgCl$_2$, 10 mM DTT, 200 µM each dNTP, 1 mM NAD, 0.035 U/µl exonuclease III, 4 U/µl Taq DNA ligase, and 0.03 U/µl AMPLITAQ GOLD®.

100 ng substrate DNA was found to be ideal for fragments between 5 kb and 8 kb in length. For larger assemblies, the amount of DNA was increased (e.g., for fragments 20 kb to 32 kb in length, 400 ng each substrate was used). Care was taken to avoid having the substrate DNA make up more than half the volume of the reaction since this was found to inhibit the reaction. Exonuclease III was used as a 1:25 dilution (in exonuclease III storage buffer) from the 100 U/µl exonuclease in concentrated enzyme stock.

The reaction was added to a thermal-cycler and assembly was performed using the following conditions: 37° C. for 5 minutes (chew-back was for at least 5 minutes at 37° C. for substrates that overlap by 40-80 bp, and 15 minutes for substrates that overlap by 300-500 bp), 75° C. for 20 minutes (heat inactivation of Exo III), cool down 0.1° C./s to 60° C. (annealing), 60° C. for 1 hour (repair), and then held at 4° C.

Figure 4A:
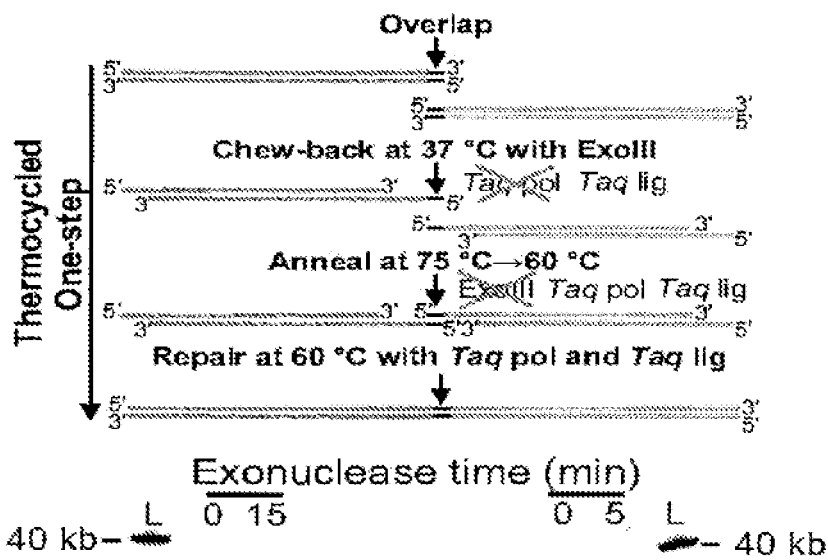
FIG. 4A is a schematic of a one-step thermocycled in vitro assembly using exonuclease III.

These steps are outlined in FIG. 4A. The results obtained from this protocol show that this method works just as well, and has all the same advantages as the two-step process with T4 DNA polymerase, Taq DNA polymerase, and Taq DNA ligase, and can be used to assemble linear or circular DNA.

Example II

Isothermal T5 Exonuclease One-Step Assembly Protocol for Nucleic Acids

An isothermal one-step assembly was developed based on the use of an isolated nonthermostable 5' to 3' exonuclease that lacks 3' exonuclease activity as follows. A reaction was set up containing the following: 100 fmol each dsDNA substrate or 3.6 pmol each ssDNA to be assembled, 16 µl 5×ISO buffer, 16 µl T5 exonuclease (0.2 U/µl, Epicentre), 8.0 µl Taq DNA ligase (40 U/µl, NEB), 1.0 µl PHUSION® DNA polymerase (2 U/µl, NEB), and water to 80 µl. The 5×ISO (ISOthermal) buffer was 25% PEG-8000, 500 mM Tris-Cl, 50 mM MgCl$_2$, 50 mM DTT, 5 mM NAD, and 1000 µM each dNTP (pH 7.5).

This gave a final concentration of 1.25 fmol/µl each dsDNA (or 45 fmol/µl each ssDNA) that was to be assembled, 5% PEG-8000, 100 mM Tris-Cl pH 7.5, 10 mM MgCl$_2$, 10 mM DTT, 200 µM each dNTP, 1 mM NAD, 0.02 U/µl T5 exonuclease, 4 U/µl Taq DNA ligase, and 0.03 U/µl PHUSION® DNA polymerase.

Methods used 1.64 µl 0.2 U/µl T5 exonuclease for substrates that overlap by 20-80 bp, and for substrates that have larger overlaps (e.g., 200 bp), 1.6 µl 1 U/µl T5 exonuclease was used. T5 exonuclease was used as a 1:50 dilution (in T5 exonuclease storage buffer) from the 10 U/µl T5 exonuclease (Epicentre) concentrated enzyme stock.

The reaction was then incubated at 50° C. for 15 minutes.

These steps are outlined in FIG. 5A. The majority of the cost to synthesize large dsDNA molecules is from the cost of the oligonucleotides. Once the cost of producing oligonucleotides drops, so will the cost to assemble large DNA molecules from oligonucleotides using the methods of the present invention.

Example III

Isothermal T5 Exonuclease One-Step Assembly Protocol for Single-Stranded Nucleic Acids Preparation of the Oligonucleotide Assembly Mixture The mixture in all kits contains the same ingredients with one exception, the presence or absence of a vector. In the absence of vector, water was substituted. The methods of the present invention allow the quick and easy use of the same assembly mixtures and buffers formulated in kits for long term storage.

A preparation of the oligonucleotide assembly mixture (for a total 120 µl volume) contains: 32 µl 5×ISO buffer, 0.064 µl 10 U/µl T5 exonuclease (Epicentre), 2 µl 2 U/µl PHUSION® polymerase (NEB), 16 µl 40 U/µl Taq ligase (NEB), 2 µl 200 ng/µl pUC19 assembly vector, and 67.94 µl water. The assembly mixture was then stored at −20° C.

A preparation of the 5×ISO buffer (for a total 6 ml volume) contains: 3 ml 1 M Tris-Cl pH 7.5 (final 0.5 M), 150 µl 2 M MgCl$_2$ (final 50 mM), 60 µl each 100 mM dGTP, dATP, dTTP, dCTP (final 1 mM each), 300 µl 1 M DTT (final 50 mM), 1.5 g PEG-8000 (final 25%), 300 µl 0.1M NAD (final 5 mM), and water to 6 ml. Concentrations in parentheses refer to the final concentration in the 5×ISO buffer.

The final concentration of all ingredients in the Oligonucleotide Assembly Mixture (mixture is 1.33× since 15 µl was added in a 20 µl final volume) was as follows: 133.33 mM Tris-Cl (pH 7.5), 13.33 mM $MgCl_2$, 266.67 µM dGTP, 266.67 µM dATP, 266.67 µM dTTP, 266.67 µM dCTP, 13.33 mM DTT, 6.67% PEG-8000, 1.33 mM NAD, 5.33 U/ml T5 exonuclease (Epicentre), 33.33 U/ml PHUSION® polymerase (NEB), 5.33 U/µl Taq Ligase (NEB), and 3.33 ng/µl pUC19 assembly vector.

The above kit, at 1.33× concentration, can be stored frozen, for at least 12 months. It can be subjected to at least ten cycles of freeze-thaw without losing activity.

Assembly of Oligonucleotides to Form a 16.5 kb Final Product Inserted into PCCIBAC Although this Example shows the assembly of ssDNA oligonucleotides, the same conditions and master mix of reagents can be used for assembling dsDNA. For example, in the first stage of assembly shown in detail here, eight single-stranded oligonucleotides are assembled to generate a double-stranded molecule of about 300 bp. The next stage, in which the 300 bp DNAs are assembled to generate larger molecules, and the subsequent stages in which those molecules are assembled to generate still larger molecules, can be accomplished by using the same master mix of reagents shown in the present example.

This Example describes a four stage assembly scheme. However, in another embodiment of the invention, 25-75 segments can be assembled at one time. In that embodiment, the number of stages is significantly reduced, e.g., down to only two.

For the first round of assembly, a mixture (pool) of eight 60 nt (60-mer) ssDNA oligonucleotides, which overlap each other by 20 bases, and which lie adjacent to one another in a known DNA to be assembled, are diluted so that there is 180 fmol/µl of each oligonucleotide in a total volume of 5 µl. This concentration was determined by the inventors to be optimal for the assembly of eight 60-mers with 20 nt overlaps. 15 µl of the 1.33× master mix as above is added to 5 µl of oligonucleotides and incubated at 50° C. for 15-60 minutes, to form a contiguous segment of dsDNA molecule of 300 bp. A pUC19 vector is present in the assembly mixture, so the 300 bp molecule is inserted into the vector.

Following assembly, the assembled molecule is transformed into a suitable *E. coli* host, and pUC19 clones are selected, using ampicillin as a selective marker. Generally, the clones are sequenced to confirm that the assembled molecule is correct. Currently, a background of incorrect sequences occurs because methods for synthesizing oligonucleotides are not accurate. It is expected that methods for correcting errors, or better methods of synthesizing the oligonucleotides, will eliminate the need for this sequencing check. For example, error-correcting enzymes or reagents can be added to or contained within the assembly reaction of the current invention. Alternatively, instead of cloning the assembled DNA molecules, they can be directly amplified by PCR, and then sequenced to confirm accuracy.

Seventy-four additional pools of eight 60-mers, from different portions of the DNA molecule to be synthesized, are also assembled. A total of 600 of these 60-mers are assembled, into a collection of 300 bp dsDNA molecules; and in subsequent rounds of assembly, the 300-mers are PCR-amplified and assembled to form 1,180 bp dsDNAs, which are in turn PCR-amplified and assembled to form 5,560-mers, which are finally assembled to form a dsDNA molecule of 16,520 bp. This molecule is then amplified (by PCR, or by a method more effective to amplify large molecules, rolling circle amplification (RCA)), cloned (e.g., into a BAC vector) and sequenced to confirm that the assembly has been accurate.

In this Example, a cloning vector is used to assemble the inserts. However, if cloning into a host organism is not required for producing more DNA molecules, since for example an in vitro method of amplification is going to be used (e.g., PCR or RCA), then the cloning vector can be absent. However, it still may be advantageous in some cases to allow the inserts to form a circle. This would allow for the incomplete assembly products (which are linear) to be removed from the complete assembly product with an exonuclease (the circle would be resistant to the exonuclease activity but the incomplete assembly products would not be.) This can be important if an in vitro method for amplification of DNA (e.g., PCR or RCA) is inhibited by the incomplete assembly products.

Use of Universal Primer Binding Sequences at the 5' and 3' Ends of Oligonucleotides to be Assembled To aid in the PCR amplification of assembled oligonucleotides, in each of the rounds of assembly, it can be advantageous to include binding domains (sites) at each end of the segments to be assembled (from ssDNA oligonucleotides) and amplified. These domains can be designed and introduced into some of the oligonucleotides (e.g., the oligonucleotides that would end up in flanking regions of the segment being built) as they are being synthesized. An exemplary dsDNA segment, in which four primer binding domains are shown, flanks the DNA molecule. In subsequent rounds of amplification and assembly, the DNAs can be PCR amplified, using "universal primers" that correspond to suitable domains, thereby eliminating the need to design separate primers for amplifying each DNA to be amplified. If desired, restriction enzyme sites (such as rare-cutter enzymes PmlI, SbfI, AscI or NotI) can also be engineered to lie between the primer binding domains. These sites can facilitate cleaving off of the primer binding sites.

One advantage of a method of the invention is that the presence of a 3' exonuclease activity during the reaction (which can be provided, e.g., by the proofreading activity of PHUSION® polymerase) will remove all of the binding domains, since these will exist as single stranded DNAs that are non-homologous to the DNAs which are being amplified. The oligonucleotides being assembled into a vector can be 40-mers instead of 60-mers. With 40-mers, there will not be a gap. The oligonucleotides being assembled can be very large (e.g., several hundred bases.) Furthermore, the oligonucleotides being assembled into the vector can be from a pool of oligonucleotides (e.g., a microchip containing 4,000 or more oligonucleotides. A microchip can serve as an inexpensive way to obtain oligonucleotides). The cloning vector does not necessarily need to be a circular one (as indicated in this figure with pUC19). Rather, it can be a linear vector with two arms (e.g., Lucigen's pJAZZ™-KA linear vector system). A linear vector may be advantageous for assembling oligonucleotides in excess without concatamerization occurring (concatamerization would lead to a single clone containing two or more sets of assembled fragments. Therefore, this would not be a pure clone which may be desired.) The cloned oligonucleotides may be transformed into *E. coli*. Individual clones containing correct assemblies can be identified by a technique such as DNA sequencing.

Assembly of Large Molecules by Automation

This method shown in this Example is readily adaptable to automation. (1) Oligonucleotides are first cloned into a vector. Currently, because of imperfect synthesis techniques, it is expected that some of the oligonucleotides will contain errors, so the initial clones must be sequenced to confirm they are correct. The initial clones can be from *E. coli* or single molecule PCR. In one embodiment of the invention, an error correction technique is employed to correct such errors; this eliminates the need to perform DNA sequencing, and allows subsequent rounds of assembly to be carried out without having to wait for the sequencing results. (2) The DNA molecules are assembled. (3) The assembled DNAs are amplified by PCR or RCA. (4) These DNAs are assembled. (5) The assembled DNAs are amplified by PCR or RCA. (6) These cycles are continued until the complete molecule is assembled. Note that RCA allows for the amplification of larger molecules than is possible with PCR, so RCA is preferred for larger piece stages of assembly. Cloning into a host organism and making more of the assembled fragments, then digesting with a restriction enzyme that can release the assembled fragments intact would be equivalent to PCR or RCA.

Example IV

Assembly of DNA Molecules Several Hundred Kilobases in Size Using Various In Vitro Methods This Example compares three assembly methods as shown in FIG. 1A (two-step thermocycled assembly with T4 pol), FIG. 4A (one-step thermocycled assembly with Exoin), and FIG. 5A (one-step isothermal assembly with T5 exo). The one-step isothermal assembly was found to be the preferred in vitro assembly method.

Method 1: Two-Step Thermocycled Assembly (with T4 Pol)

A 4× chew-back and anneal (CBA) reaction buffer (20% PEG-8000, 800 mM Tris-HCl pH 7.5, 40 mM $MgCl_2$, 4 mM DTT) was used for thermocycled DNA assembly. DNA molecules were assembled in 20 µl reactions consisting of 5 µl 4×CBA buffer, 0.2 µl of 10 mg/ml BSA (NEB), and 0.4 µl of 3 U/µl T4 pol (NEB). T7 pol can be substituted for T4 pol. Approximately 10-100 ng of each ~6 kb DNA segment was added in equimolar amounts. For larger DNA segments, increasingly proportionate amounts of DNA were added (e.g., 250 ng of each 150 kb DNA segment). Assembly reactions were prepared in 0.2 ml PCR tubes and cycled as follows: 37° C. from 0 to 18 minutes, 75° C. for 20 minutes, cooled 0.1° C./s to 60° C., held at 60° C. for 30 minutes, then cooled to 4° C. at a rate of 0.1° C./s. In general, a chew-back time of 5 minutes is used for overlaps less than 80 bp and 15 minutes for overlaps greater than 80 bp. Ten µl of the CBA reactions were then added to 25.75 µl of Taq repair buffer (TRB), which consists of 5.83% PEG-8000, 11.7 mM $MgCl_2$, 15.1 mM DTT, 311 µM each of the 4 dNTPs, and 1.55 mM $NAD^+$. Four µl of 40 U/µl Taq lig (NEB) and 0.25 µl of 5 U/µl Taq pol (NEB) were added and the reactions were incubated at 45° C. for 15 minutes. For the T4 pol fill-in assembly method, 10 µl of the CBA reaction is mixed with 0.2 µl of 10 mM dNTPs and 0.2 µl of 3 U/µl T4 pol. This reaction was carried out at 37° C. for 30 minutes.

Results: Step 1: Chew-back and anneal. The prior art 2-step in vitro recombination method for assembling overlapping DNA molecules makes use of the 3' exonuclease activity of T4 DNA polymerase (T4 pol) to produce ssDNA overhangs, and a combination of Taq DNA polymerase (Taq pol) and Taq DNA ligase (Taq lig) to repair the annealed joints. To better understand the kinetics of this reaction, 8 DNA molecules, each ~6 kb and overlapping by ~300 bp, were exposed to T4 pol at 37° C. for up to 18 minutes. Samples were removed every 2 minutes and annealed. Following a 10 minute exonuclease reaction, the majority of the input DNA was annealed, and the predicted ~48 kb full-length product is observed. These reactions require the presence of PEG-8000, a reagent that induces macromolecular crowding (see FIG. 1B).

Figure 1C:
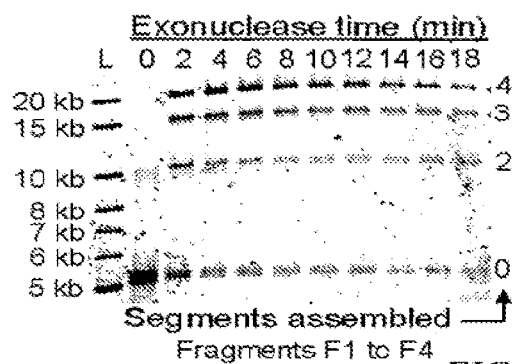
FIG. 1C shows the results of assembly of 4 nucleic acid fragments, each 5 kb, with 40 bp overlapping sequences, in the presence of PEG-8000, using the method shown in FIG. 1A.
Figure 1B:
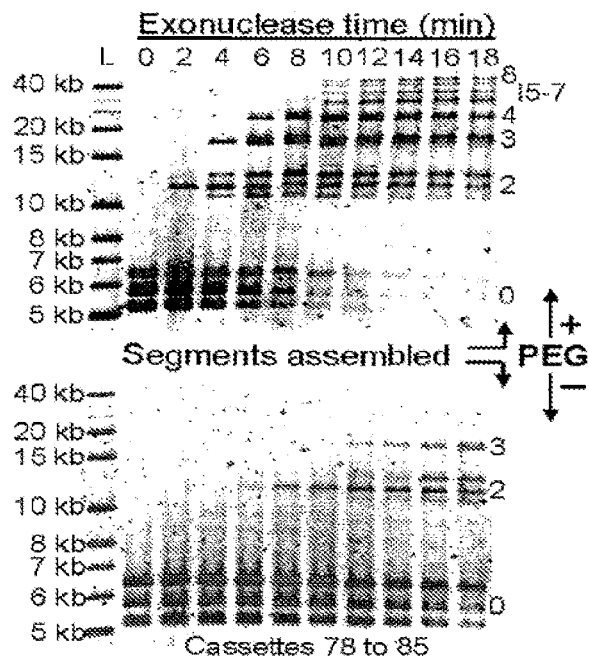
FIG. 1B shows the results of assembly of 8 nucleic acid fragments, each between 5.3 kb and 6.5 kb, with 240 to 360 bp overlapping sequences, carried out in the presence (+) or absence (−) of 5% PEG-8000, using the method shown in FIG. 1A.

Assembling DNA molecules with significantly smaller overlaps than 300 bp would have several advantages. When synthetic DNA fragments are joined, smaller overlaps would reduce the overall cost of synthesis. Additionally, small overlaps can be added to PCR primers. For these reasons, it was determined whether DNA molecules with only 40 bp overlaps could be assembled. The assembly reaction in FIG. 1A was performed using 4 DNA molecules, each 5 kb in length, and overlapping by 40 bp. Following a 2 minute exposure to T4 pol, all 4 DNA molecules were efficiently assembled into the full-length 20 kb product (FIG. 1C).

Figure 1D:
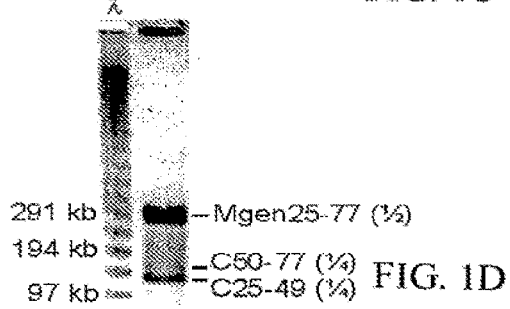
FIG. 1D shows the results of assembly of a *Mycoplasma genitalium* one-half genome (310 kb), from two one-quarter genome fragments, 144 kb and 166 kb, with 257 bp overlapping sequences.
Figure 1E:
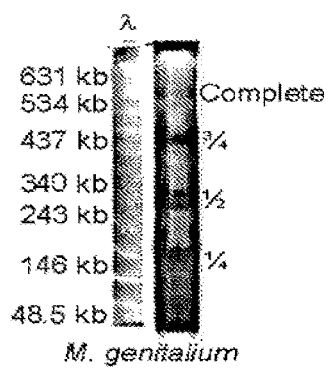
FIG. 1E shows the results of assembly of the complete synthetic *Mycoplasma genitalium* genome from four one-quarter genome fragments, ~150 kb each with 80 to 257 bp overlapping sequences.

It was next determined whether significantly larger DNA molecules could be joined by this method. Two XA molecules of the synthetic *M. genitalium* genome, C25-49 (144 kb) and C50-77 (166 kb), with a 257 bp overlap, were reacted with T4 pol for 15 minutes and annealed, then analyzed by field-inversion gel electrophoresis (FIGE) (FIG. 1D). They were efficiently assembled into the 310 kb product (Mgen25-77). Further, when all 4 quarter molecules were reacted under the same conditions, the full-length synthetic *M. genitalium* genome (~583 kb) is assembled (FIG. 1E).

Results: Step 2: Repairing the assembled molecules. Taq pol is a preferred gap-filling enzyme since it does not strand-displace, which would lead to disassembly of the joined DNA fragments. It also has inherent 5' exonuclease activity (or nick translation activity), which eliminates the need to phosphorylate the input DNA (a requirement for DNA ligation). This is because 5'-phosphorylated ends are created following nick translation. Further, this activity removes any non-complementary sequences (e.g., partial restriction sites), which would otherwise end up in the final joined product.

To verify that assembled DNA molecules have been successfully repaired, dsDNA products can be denatured at 94° C. in the presence of formamide and analyzed by agarose gel electrophoresis (FIG. 2A). Repair was assessed for 2 pairs of ~5-6 kb DNA molecules with 40 bp or 300 bp overlaps. In each case, similar results were obtained (FIG. 2B). Assembled, but unrepaired DNA molecules (lane 1) are denatured to ssDNA input in the presence of formamide (lane 2). In the absence of Taq lig, the nicks are not sealed and the 5' exonuclease activity of Taq pol eliminates the overlapping DNA sequence, leading to disassembly of the DNA molecules (compare lanes 3 and 4). In the presence of Taq lig (lane 5), the nicks are sealed and a higher molecular weight ssDNA product is observed (lane 6). Thus, dsDNA molecules, with as little as 40 bp overlaps, were covalently joined by this assembly method.

Introduction of errors during DNA assembly. During in vitro recombination, mutations may be introduced in the assembled DNA. The first source for mutations is from Taq pol, which incorporates an incorrect nucleotide approximately once every 4000 nt. The second source for mutations is from the primers used to PCR-amplify the bacterial artificial chromosomes (BACs). Both of these error types were observed when 30 assembled molecules were cloned and sequenced during the synthesis of the *M. genitalium* genome. However, of the 210 repaired junctions, there was only 1 error that likely resulted from BAC PCR. Remarkably, there were only 3 errors that can be attributed to inaccurate gap fill-in by Taq pol.

Assembly methods that employ a repair step to produce covalently sealed circular DNA molecules allow for the possibility of RCA (e.g., amplification by phi29 polymerase). This is not the case for assembly methods that omit a repair step. To demonstrate this, 4 fragments, F5 (1020 bp), F6, (1040 bp), F7 (2379 bp), and F8 (3246 bp), each with 40 bp overlaps, were joined into a 7525 bp circle. (FIG. 3) As expected, only repaired assembled products could be amplified by phi29 polymerase.

Method 2: One-Step Thermocycled Assembly (with Exo III)

A 4× chew-back, anneal, and repair (CBAR) reaction buffer (20% PEG-8000, 600 mM Tris-HCl pH 7.5, 40 mM $MgCl_2$, 40 mM DTT, 800 µM each of the 4 dNTPs, and 4 mM $NAD^+$) was used for one-step thermocycled DNA assembly. DNA molecules (added in amounts described above for CBA reactions) were assembled in 40 µl reactions consisting of 10 µl 4×CBAR buffer, 0.35 µl of 4 U/µl ExoIII (NEB), 4 µl of 40 U/µl Taq lig, and 0.25 µl of 5 U/µl Ab-Taq pol (Applied Biosystems). ExoIII was diluted 1:25 from 100 U/µl in its stored buffer (50% Glycerol, 5 mM KPO4, 200 mM KCl, 5 mM 2-Mercaptoethanol, 0.05 mM EDTA, and 200 µg/ml BSA, pH 6.5). DNA assembly reactions were prepared in 0.2 ml PCR tubes and cycled using the following conditions: 37° C. for 5 or 15 minutes, 75° C. for 20 minutes, cool down 0.1° C./s to 60° C., then held at 60° C. for 1 hour. In general, a chew-back time of 5 minutes was used for overlaps less than 80 bp and 15 minutes for overlaps greater than 80 bp. ExoIII is less active on 3' protruding termini, which can result from digestion with certain restriction enzymes. This can be overcome by removing the overhangs to form blunt ends with the addition of T4 pol and dNTPs, as described above, prior to assembly.

Results: A DNA assembly method that requires the absence of dNTPs to achieve exonuclease activity, such as the T4 pol-based system described above, cannot be completed in one-step. This is because dNTPs are required at a later point to fill-in the gapped DNA molecules. Exonuclease III (ExoIII), which removes nucleotides from the 3' ends of dsDNA, is fully functional even in the presence of dNTPs so it is a candidate for a 1-step reaction. However, it will compete with polymerase for binding to the 3' ends. To eliminate this competition, and allow for 1-step DNA assembly, antibody-bound Taq pol (Ab-Taq pol) was used in combination with ExoIII (FIG. 4A). In this assembly method, overlapping DNA fragments and all components necessary to covalently join the DNA molecules (i.e., ExoIII, Ab-Taq pol, dNTPs, and Taq lig) were added in a single tube, and placed in a thermocycler. At 37° C., ExoIII is active (but Ab-Taq pol remains inactive) and recesses the 3' ends of the dsDNA molecules. The reaction was then shifted to 75° C., which inactivates ExoIII. Annealing of the DNA molecules commences and the antibody dissociates from Taq pol, thus activating this enzyme. Further annealing, extension, and ligation is then carried out at 60° C.

Figure 4B:
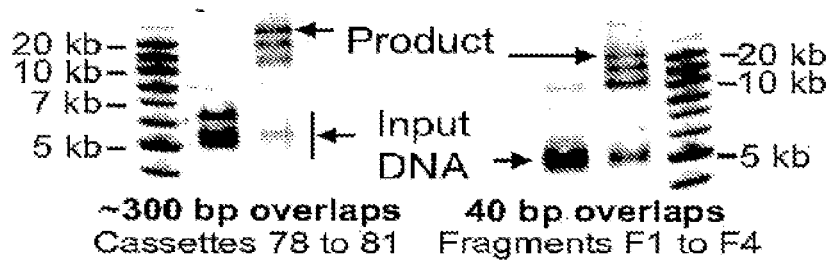
FIG. 4B shows the results of 2 assemblies of 4 different nucleic acid fragments, each ~5 kb with either 300 bp or 40 bp overlapping sequences, using the method shown in FIG. 4A.
Figure 4C:
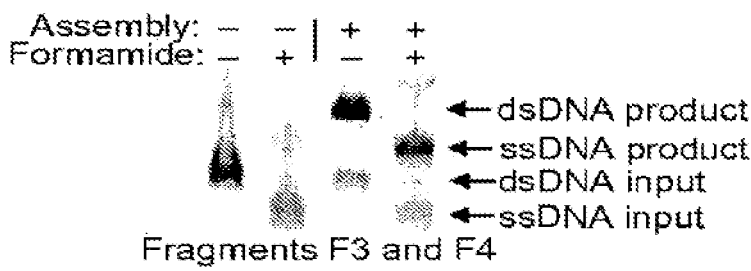
FIG. 4C shows the results of analyzing the repair of the assembly products, as shown in FIG. 2A.

As shown in FIG. 4B, four 5 to 7 kb DNA molecules with 40 bp overlaps or ~300 bp overlaps can be efficiently assembled. Cassettes 78 to 81 (240 bp to 300 bp overlaps) and fragments F1 to F4 (40 bp overlaps) are assembled and then analyzed by U-5 FIGE. The completely assembled product and unreacted input DNA are indicated with arrows. To demonstrate that the joined DNA molecules are repaired by this method, assembly products were denatured in the presence of formamide and analyzed on agarose gels. The DNA molecules were efficiently assembled and repaired. As indicated in FIG. 4C, Fragments F3 and F4 were reacted as described in the presence (+ Assembly) or absence (− Assembly) of ExoIII. Repair is assessed by denaturation of the dsDNA molecules in the presence (+) or absence (−) of formamide as described in FIG. 2A.

Method 3: One-Step Isothermal Assembly (with T5 Exo)

A 5× isothermal (ISO) reaction buffer (25% PEG-8000, 500 mM Tris-HCl pH 7.5, 50 mM $MgCl_2$, 50 mM DTT, 1 mM each of the 4 dNTPs, and 5 mM $NAD^+$) was used for one-step DNA isothermal assembly at 50° C. DNA molecules (added in amounts described above for CBA reactions) were assembled in 40 µl reactions consisting of 8 µl 5×ISO buffer, 0.8 µl of 0.2 U/µl or 1.0 U/µl T5 exo (Epicentre), 4 µl of 40 U/µl Taq lig, and 0.5 µl of 2 U/µl PHUSION® pol (NEB). T5 exo was diluted 1:50 or 1:10 from 10 U/µl in its stored buffer (50% glycerol, 50 mM Tris-HCl pH 7.5, 0.1 mM EDTA, 1 mM DTT, 0.1 M NaCl, and 0.1% TRITON® X-100) depending on the overlap size. For overlaps shorter than 150 bp, 0.2 U/µl T5 exo is used. For overlaps larger than 150 bp, 1.0 U/µl T5 exo is used. All isothermal assembly components can be stored at −20° C. in a single mixture at 1.33× concentration for more than one year. The enzymes are still active after more than 10 freeze-thaw cycles. To constitute a reaction, 5 µl DNA is added to 15 µl of this mixture. Incubations are carried out at 50° C. for 15 to 60 minutes, with 60 minutes being optimal.

Protocol for this DNA assembly system, including how to prepare an assembly master mixture: 1. Prepare 5×ISO buffer. Six ml of this buffer can be prepared as follows: 3 ml of 1 M Tris-HCl pH 7.5, 150 µl of 2 M MgCl2, 60 µl of 100 mM dGTP, 60 µl of 100 mM dATP, 60 µl of 100 mM dTTP, 60 µl of 100 mM dCTP, 300 µl of 1 M DTT, 1.5 g PEG-8000, 300 µl of 100 mM $NAD^+$. Add water to 6 ml, aliquot 100 µl and store at −20° C. 2. Prepare an assembly master mixture. This can be prepared as follows: 320 µl 5×ISO buffer, 0.64 µl of 10 U/µl T5 exo (Epicentre), 20 µl of 2 U/µl PHUSION® pol (NEB), and 160 µl of 40 U/µl Taq lig (NEB). Add water to 1200 aliquot 15 µl and store at −20° C. This is ideal for the assembly of DNA molecules with 20-150 bp overlaps. For DNA molecules overlapping by larger than 150 bp, use 3.2 µl of 10 U/µl T5 exo. 3. Thaw a 15 µl assembly mixture aliquot and keep on ice until ready to be used. 4. Add 5 µl of DNA to be assembled to the master mixture. The DNA should be in equimolar amounts. Use 10-100 ng of each ~6 kb DNA fragment. For larger DNA segments, increasingly proportionate amounts of DNA should be added (e.g., 250 ng of each 150 kb DNA segment). 5. Incubate at 50° C. for 15-60 minutes (60 minutes is optimal).

Results: Exonucleases that recess dsDNA from 5' ends, and are not inhibited by the presence of dNTPs, are also candidates for one-step DNA assembly reactions. Further, these exonucleases will not compete with polymerase activity. Thus, all activities required for DNA assembly can be simultaneously active in a single isothermal reaction. A 50° C. isothermal assembly system was optimized using the activities of the 5'-T5 exonuclease (T5 exo), PHUSION® DNA polymerase (PHUSION® pol), and Taq lig (FIG. 5A). Taq pol can be used in place of PHUSION® pol; however, PHUSION® pol is preferable since it has inherent proofreading activity for removing non-complementary sequences from assembled molecules. Further, PHUSION® pol has a significantly lower error rate (New England Biolabs). To test this system, 2 restriction fragments overlapping by ~450 bp were cleaved from the 6 kb pRS415 vector and reassembled into a circle (FIG. 5B). Following 8 minutes at 50° C., the linear substrate DNA is completely reacted and/or degraded, and the major product is the 6 kb circle, which migrated just below the 4 kb linear position on a 0.8% agarose gel. T5 exo becomes inactive, and no longer participates in DNA assembly following incubation at 50° C. for 12 minutes. T5 exo actively degrades linear DNA molecules; however, closed circular DNA molecules are not degraded. The circularity of this assembled product is confirmed by treating with additional T5 exo (FIG. 5B). To demonstrate that this assembled product is the predicted 6 kb circle, it was digested with NotI (a single-cutter). The 6 kb linear fragment was then observed (FIG. 5C). Thus, DNA molecules can be assembled and repaired in a single, isothermal step using this method.

It was next shown that molecules with 40 bp overlaps could also be joined. This was accomplished if the concentration of T5 exo was reduced (FIG. 5D). Three 5 kb DNA fragments, F1 to F3, were efficiently assembled into BAC-F1/F3 (~8 kb). Further, when the assembled DNA molecules from the 4 U/ml T5 exo reaction were transformed into *E. coli*, 450 colonies were obtained and 9 out of 10 colonies had the predicted 15 kb insert (FIG. 5E).

General Accessory Methods

Preparation of DNA molecules for in vitro recombination. The DNA molecules used in the assembly analyses are derived from several sources including (i) the assembly intermediates of the synthetic *M. genitalium* genome, (ii) PCR products derived from plasmids (F6 and F8), *Clostridium cellulolyticum* genomic DNA (F1 to F4), and *Mycoplasma gallisepticum* genomic DNA (F5 and F7), and (iii) pRS415 restriction fragments. In some instances, DNA fragments were extracted from agarose gels; however, in general this is not necessary. DNA molecules were dissolved or eluted with Tris/EDTA (TE) buffer pH 8.0 and quantified by agarose gel-electrophoresis with standards. Specific protocol used was as follows:

*E. coli* strains carrying each of *M. genitalium* cassette number 66 to 69 (contained in pENTR223), each of *M. genitalium* cassette number 78 to 85 (contained in pBR322), C1-24, C25-49, C50-77, C78-101 (each contained in pCC1BAC), or pRS415 were propagated in LB medium containing the appropriate antibiotic and incubated at 30° C. or 37° C. for 16 hours. The cultures were harvested and the DNA molecules were purified using Qiagen's HiSpeed Plasmid Maxi Kit according to the instructions provided, with the exception of C-assemblies, which were not column-purified. Instead, following neutralization of the lysed cells, C-assemblies were centrifuged then precipitated with isopropanol. DNA pellets were dissolved in Tris/EDTA (TE) buffer then RNAse treated, phenol-chloroform extracted, and ethanol precipitated. DNA pellets were dissolved in TE buffer. Cassettes 66 through 69 and 78 through 85 were excised from the vectors by restriction digestion with either FauI or BsmBI, and C-assemblies were excised by digestion with NotI. To generate the 4024 bp and 2901 bp overlapping fragments of pRS415, DNA was digested with PvuII and ScaI, or PsiI, respectively. Restriction digestions were terminated by phenol-chloroform extraction and ethanol precipitation. DNA was dissolved in TE buffer pH 8.0 then quantified by gel electrophoresis with standards. Fragments F1 to F8 were generated by PCR using the PHUSION® Hot Start High-Fidelity DNA polymerase with HF Buffer (NEB) according to the instructions provided. PCR products were extracted from agarose gels following electrophoresis and purified using the QIAQUICK® Gel Extraction Kit (Qiagen) according to the instructions provided, except DNA was eluted from the columns with TE buffer pH 8.0.

Fragments F1 to F4 were amplified from *Clostridium cellulolyticum* genomic DNA using primers
F1-For
(SEQ ID NO: 1)
(GCAGCTTCAAGTCCTGCAAACAAGGTGTACCAGGATCGTT)
and F1-Rev
(SEQ ID NO: 2)
(GATTTCAGTGTAGTTAGGGCCAGTTGAATTCAAACCTGCC);

F2-For
(SEQ ID NO: 3)
(GGCAGGTTTGAATTCAACTGGCCCTAACTACACTGAAATC)
and

F2-Rev
(SEQ ID NO: 4)
(CTTGGTGCCATCAGCATTGTTCTCTGTACCGCCCACTGTC);

F3-For
(SEQ ID NO: 5)
(GACAGTGGGCGGTACAGAGAACAATGCTGATGGCACCAAG)
and

F3-Rev
(SEQ ID NO: 6)
(CAGTTGAATAATCATGTGTTCCTGCGGCAAATGCAGTACC);
and

F4-For
(SEQ ID NO: 7)
(GGTACTGCATTTGCCGCAGGAACACATGATTATTCAACTG)
and

F4-Rev
(SEQ ID NO: 8)
(TTATTTACCAAGAACCTTTGCCTTTAACATTGCAAAGTCA),
respectively.

F5 and F7 were amplified from *Mycoplasma gallisepticum* genomic DNA using primers
F5-For
(SEQ ID NO: 9)
(GCTTGCATGCATCCTGTTTATTCATCACAAACATTGAAC)
and F5-Rev
(SEQ ID NO: 10)
(AATTCTGCAGTTTTTATTTCCTAACAGAACATTTTTTCTAGTATAGC);
and F7-For
(SEQ ID NO: 11)
(CGACTCTAGATAAATAGCCTTTCTTTATCTTTTTGAGGC)
and F7-Rev
(SEQ ID NO: 12)
(CCGGGGATCCCTTTCTCAATTGTCTGCTCCATATATGTT),
respectively.

F6 and F8 were amplified from pRST21 using primers
F6-For
(SEQ ID NO: 13)
(TAGAAAAAATGTTCTGTTAGGAAATAAAAACTGCAGAATTAAAAGTTAGT GAACAAGAAAAC)
and F6-Rev
(SEQ ID NO: 14)
(AGCCTCAAAAAGATAAAGAAAGGCTATTTATCTAGAGTCGACCTGCAGTT CAGATC);
and F8-For
(SEQ ID NO: 15)
(TGTTCAATGTTTGTGATGAATAAACAGGATGCATGCAAGCTTTTGTTCCC TTTAG)
and F8-Rev
(SEQ ID NO: 16)
(AAACATATATGGAGCAGACAATTGAGAAAGGGATCCCCGGGTACCGAGCT C),
respectively.

Rolling circle amplification (RCA) of assembled products. RCA was carried out as previously described. One μl of the repaired or unrepaired reaction was mixed with 1 µl of 100 mM NaOH and incubated at room temperature for 5 minutes to denature the double-stranded DNA. One µl of this alkaline-treated mixture was then added to 19 µl of RCA components in a 0.2 ml PCR tube. The final reaction concentrations for RCA are as follows: 37 mM Tris-HCl pH 7.5, 50 mM KCl, 10 mM MgCl$_2$, 5 mM (NH$_4$)$_2$SO$_4$, 100 µg/ml BSA, 1 mM DTT, 3.25 mM random hexamers (Fidelity System MD), 1 U/ml yeast pyrophosphatase (United States Biochemical), and 250 U/ml phi29 DNA polymerase (NEB). The reaction was incubated at 30° C. for 20 hours, and then terminated by incubation at 65° C. for 10 minutes.

Cloning the DNA assembly products. To clone assembled products, reactions were carried out in the presence of PCR-amplified BACs containing 40 bp of overlapping sequence to the ends of the assembled product. NotI restriction sites were also included to allow release of the vector. In general, pCC1BAC™ was used. However, for cloning Mgen25-77, a version of pCC1BAC™, named KanBAC, was constructed that contains the kanamycin resistance gene in place of the chloramphenicol resistance gene. Samples (up to 1 µl) of the assembly reactions were transformed into 30 µl TRANSFORMAX™ EPI300™ (Epicentre) electrocompetent E. coli cells in a 1 mm cuvette (BioRad) at 1200 V, 25 µF, and 200 O using a Gene Pulser XCELL™ Electroporation System (BioRad). Cells were allowed to recover at 30° C. or 37° C. for 2 hours in 1 ml SOC medium then plated onto LB medium+12.5 µg/ml chloramphenicol or LB medium+25 µg/ml kanamycin. Following incubation at 30° C. or 37° C. for 24 to 48 hours, individual colonies were selected and grown in 3 ml LB medium+12.5 µg/ml chloramphenicol or 25 µg/ml kanamycin overnight at 30° C. or 37° C. DNA was prepared from these cells by alkaline-lysis using the P1, P2, and P3 buffers supplied by Qiagen then isopropanol precipitation. DNA pellets were dissolved in TE buffer pH 8.0 containing RNAse then digested with NotI to release the insert from the BAC.

Agarose gel analyses of assembled DNA molecules and cloned products. U-5 FIGE analysis was performed on 0.8% E-gels (Invitrogen, catalog #G5018-08) and the parameters are forward 72 V, initial switch 0.1 sec, final switch 0.6 sec, with linear ramp and reverse 48 V, initial switch 0.1 sec, final switch 0.6 sec, with linear ramp. U-2 FIGE analysis was performed on 1% Agarose gels (BioRad, catalog #161-3016) in 1×TAE buffer with 0.5 µg/ml ethidium bromide without circulation and the parameters are forward 90 V, initial switch 5.0 sec, final switch 30 sec, with linear ramp, and reverse 60 V, initial switch 5.0 sec, final switch 30 sec, with lineal-ramp. DNA bands were visualized with a BioRad Gel Doc or an Amersham Typhoon 9410 Fluorescence Imager.

Example V

Comparison of the Three DNA Assembly Methods

This Example compares the efficacy of the three different in vitro assembly methods as shown in FIG. 1A (two-step thermocycled assembly with T4 pol), FIG. 4A (one-step thermocycled assembly with ExoIII), and FIG. 5A (one-step isothermal assembly with T5 exo).

Efficiency of Assembly of a 31 kb Fragment

In step (a), shown in FIG. 6A, cassettes 66 to 69 (5.9 kb to 6.2 kb with 80 bp overlaps) were assembled into BAC66-69 (~8 kb with 40 bp overlaps), as shown in FIG. 1A, without repair (CBA), with complete repair (CBA+TRB), or with gap fill-in repair with T4 pol but without ligation (T4 pol fill-in), and as shown in FIG. 4A (ExoIII) and FIG. 5A (T5 exo). Equal amounts were analyzed by U-5 FIGE then transformed into E. coli.

Then, in step (b), as shown in FIG. 6B, a 0.1 µl sample of the assembly reactions of step (a) yielded the number of transformants noted. For each assembly method, DNA was extracted from 10 transformants and digested with NotI for determination of correct insert size (~23 kb, denoted by *).

Efficiency of Assembly of a 310 kb Fragment

In step (c), shown in FIG. 6C, two one-quarter M. genitalium genomes C25-49 and C50-77 were assembled into BAC25-77 (~8 kb with 40 bp overlaps) using the methods described in (a). A fraction of each was analyzed by U-2 FIGE. In step (d), as shown in FIG. 6D, equal amounts were transformed into E. coli, and a 1 µl sample of the assembly reactions in (c) yielded the number of transformants noted. No transformants were obtained for the CBA and T4 pol fill-in reactions so analysis ended at that step. DNA was prepared from 7 to 10 transformants of each assembly method, then digested with NotI for determination of correct insert size (~310 kb, denoted by †).

Cloning of assembled DNA molecules is a common application of these methods. Thus, it is important to determine which assembly method was best for cloning. First, the joining efficiencies of synthetic M. genitalium cassettes 66 to 69 (~6 kb each and with 80 bp overlaps) into a BAC with 40 bp overlaps to the ends of the assembly were compared. Also included was a comparison with 2 additional DNA assembly systems that omit fill-in and ligation steps. Each of these 5 methods efficiently and similarly assembled cassettes 66 to 69 into BAC66-69 as determined by FIGE (FIG. 6A). Equal amounts of these DNA molecules were then transformed into E. coli. Ten randomly selected clones from each method were analyzed following NotI digestion, which released the vector from the ~23 kb insert (FIG. 6B). For each method, 90 to 100% of the clones had the correct insert. Omitting both DNA polymerase and ligase yields only 2% of the number of colonies achieved with complete repair. This emphasizes the importance of a repair step. Leaving the nicks unsealed but filling in the gaps increases the cloning efficiency to 44% of the complete reaction, suggesting that gaps can significantly influence cloning efficiencies in E. coli.

In prior work during the construction of the synthetic M. genitalium genome, the DNA assembly strategy shown in FIG. 1A to clone ½ genomes from ¼ molecules in E. coli could not be used. The assembly was repeated with the novel in vitro methods of the present invention to determine if any of these assembly methods can be used to clone Mgen25-77 (310 kb) from C25-49 and C50-77. Each method efficiently joined the 310 kb, half M. genitalium genome (FIG. 6C). As expected, this DNA molecule could not be cloned in E. coli using the strategy outlined in FIG. 1A. Filling in the gaps with T4 pol, but leaving the nicks unsealed, does not produce transformants. However, the one-step ExoIII- and T5 exo-based systems of the present invention were successfully used to clone these large DNA molecules (FIG. 6D). Thus, there are 2 preferred DNA assembly systems as described in the present invention that can be used to efficiently join and clone DNA molecules up to several hundred kb in length in E. coli, the approximate upper limit for transformation into this bacterium.

Example VI

Assembly of Large DNA Molecules

Invention methods were capable of assembling DNA molecules of unprecedented sizes. The complete synthetic ~583 kb *M. genitalium* genome was assembled in vitro. It is well known that DNA molecules become more fragile as they get larger. The success in assembling such large molecules may be attributed to the presence of PEG in these reactions. The viscosity of this reagent may reduce shear forces on these large molecules in solution. The size limit for in vitro DNA assembly is not known; however, products as large as 900 kb have been observed for each of the assembly methods. These methods may provide sufficient amounts of recombined product for an intended application. If not, the assembled product may be propagated in a host organism. However, assembled DNA molecules of ~300 kb have only been cloned in *E. coli* by the one-step assembly methods and not by the two-step method. One explanation is that reducing reaction manipulation reduces DNA damage, and thus more intact clones are obtained. Once better in vitro amplification tools are developed (e.g., RCA), it may no longer be required to replicate the assembled constructs in a host organism. However, currently the largest phi29 products reported are only ~70 kb.

Although several recombination methods are provided herein, the one-step isothermal system is preferred due to its simplicity. All components of this assembly system can be premixed and kept frozen until needed. Thus, all that is required for DNA assembly is for input DNA to be added to this mixture, and the mixture to be briefly incubated at 50° C. This approach could be very useful for cloning multiple inserts into a vector without relying on the availability of restriction sites, and for rapidly constructing large DNA molecules. For example, regions of DNA too large to be amplified by a single PCR event can be divided into multiple overlapping PCR amplicons and then assembled into one piece. The isothermal system is advantageous for assembling circular products, which accumulate because they are not substrates for any of the 3 enzymes. The one-step-thermocyled method, on the other hand, can be used to generate linear assemblies since the exonuclease is inactivated during the reaction.

Example VII

Codon Optimization

The methods of the present invention can be used to optimize codon usage in accordance with the host cell to construct a gene that has the optimal protein yield. Often, the gene that yields the highest amount of protein gives the optimal yield. However, if the gene is toxic to the host cell that produces the gene, the optimal yield may be lower than the highest yield.

Codons of a gene are computationally optimized to produce a single sequence of the full gene. This single sequence may not be the very best to produce an optimal yield, but serves as a starting point. Next, oligonucleotides are generated computationally such that the codon choices at selected positions are varied. As shown in FIG. 7A, the oligonucleotides may encompass more than one codon, but within each oligonucleotide at least one codon is varied. For instance, three different codons encoding leucine are present in three versions of "Oligo 1". The oligonucleotides overlap with one another in order to allow for assembly according to the methods described herein.

A sufficient number of oligonucleotides is used to assemble the entire gene. When the oligonucleotides are assembled according to an assembly reaction, such as any of the above-described assembly reactions, a gene library is produced such that each member contains a particular combination of codon variants. Every member of the library, however, yields the same amino acid sequence. The method thus allows for optimization of translation of the gene product to provide the same polypeptide, according to the preferences of the chosen host. Individual clones can be assayed for native protein yield, with the clone producing the optimal yield selected.

Example VIII

Gene Optimization

The methods of the present invention can be used to provide a protein that has maximum activity. The protein with maximum activity is comprised of a consensus sequence from a group of homologous protein sequences. FIG. 7B depicts five homologous proteins that each contain three motifs and one domain. For instance, protein 1 may be from human, protein 2 from *C. elegans*, protein 3 from *S. cerevisiae*, protein 4 from mouse, and protein 5 from *D. melanogaster*. A consensus protein has motif A from protein 5, motif B from protein 2, domain A from protein 1 and motif C from protein 3.

Synthetically, one can generate a library of protein variants by putting together different combinations of the motif and domain protein blocks from a set of homologous proteins. In the scheme of FIG. 7B, diversity or library complexity is five to the fourth power, or 625 unique clones that can be tested for maximum activity. The motif and domain protein blocks may be synthesized according to any of the methods of the previous examples. Then, library clones may be screened for maximum protein activity.

Example IX

Pathway Optimization and Assembly of a Combinatorial Library

The methods of the present invention can be used to combine multiple versions of each gene in a pathway, which are randomly assembled to produce a combinatorial pathway library, as shown in FIG. 1C. The products of all of the in vitro assembly reactions are then cloned into an appropriate recipient cell, and the cells then assayed for yield of the specific product or characteristic of the pathway.

The versions of each gene may homologues from multiple species or synthetically generated variants according to the previous examples. The genes may include upstream promoter elements that vary from one species to the next, such that optimum yield can be obtained from pathways involving transcription factors.

These methods allow the possibility of screening for enormous variant pathways that heretofore would have been impossible to synthesize individually. For example, a combinatorial library of 10⁹ variant pathways can be constructed from 90 individual genes (10 variants of each of nine genes in the pathway). The genes are synthesized individually, but the pathways are combinatorially assembled efficiently and quickly in vitro. Each gene is flanked by a joining sequence that provides an overlap with any variant of the adjacent pathway genes (or with the vector in the case of the first and last pathway genes). All 90 genes are pooled along with the vector and joined by the assembly reactions of the present invention to produce the combinatorial library.

Example X

Figure 8A:
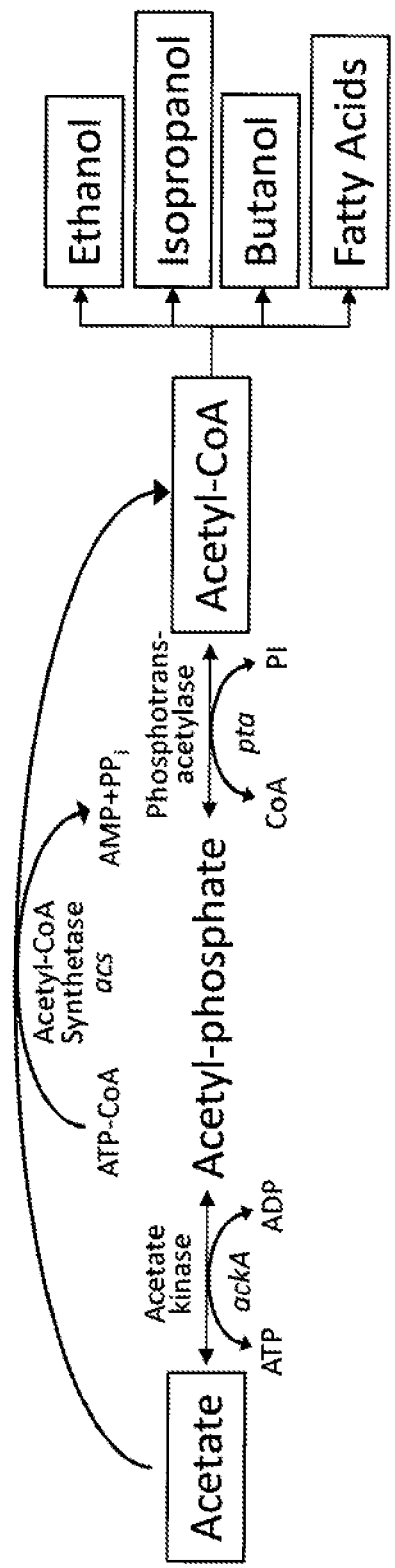
FIG. 8A is a schematic of an acetate utilization pathway.

Assembly of a Combinatorial Library to Optimize an Acetate Utilization Pathway The methods of the present invention were used to create a combinatorial library of synthetically made orthologs to the acetate kinase ackA gene and the phosphostransacetylase pta gene in *E. coli* in order to optimize the acetate utilization (ackA/pta) pathway. The ackA/pta pathway in *E. coli* enables growth on acetate as a carbon source. Both genes mediate the interconversion between acetate and acetyl-CoA, as shown in FIG. 8A. Acetate kinase (ackA) converts acetate plus ATP to acetyl-phosphate. Phosphtransacetylase (pta) converts acetyl-phosphate and CoA to acetyl-CoA. *E. coli* produces substantial amounts of acetate during excess glucose fermentation in high density cultures, and acetate is the major byproduct under aerobic conditions. High acetate concentration inhibits growth because it decouples transmembrane pH gradients, which in turn negatively affects internal osmotic pressure, pH, and amino acid synthesis. In addition, the acid pretreatment of biomass releases substantial amounts of acetate (derived from the acetyl side chains of hemicellulose). The methods described in this Example show the use of combinatorial optimization to boost acetate utilization by the host cells to eliminate excess acetate and enhance growth of the host. A strain of *E. coli* was developed that was not inhibited by the presence of acetate when grown in a glucose-salts minimal medium, and could grow vigorously on acetate as the sole carbon source.

Figure 8B:
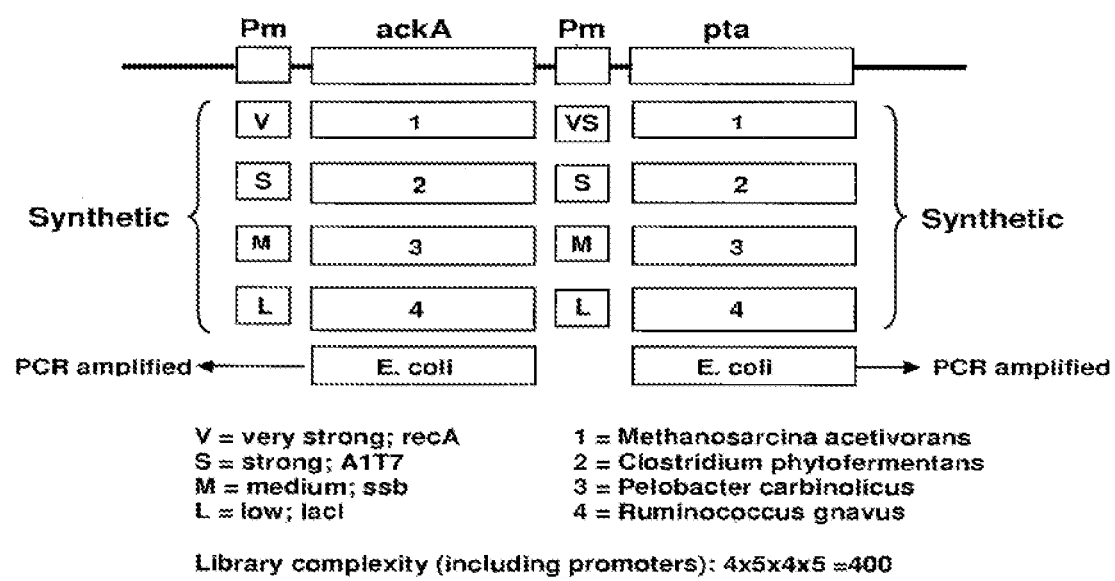
FIG. 8B is a schematic illustrating the use of variant genes from 5 organisms together with 4 control sequences to create a combinatorial library of the acetate utilization pathway shown in FIG. 8A.

Variants of the ackA and pta genes were combinatorially placed under independent promoter control. The library was constructed from synthetic orthologs to both genes from five different organisms with four different promoters for each gene, as shown in FIG. 8B. The organisms are *Methanosarcina acetivorans*, *Clostridium phytofermentans*, *Pelobacter carbinolicus*, *Ruminococcus ignavus*, and *E. coli*. The four promoters have different strengths, as indicated by VS (very strong; recA), S (strong; A1 T7), M (medium; ssb), and L (low; lad). All the valiant pieces were made synthetically by Integrated DNA Technologies (IDT). The complexity of the library (total number of combinatorial constructs) was 400 (4×5×4×5).

Figure 8C:
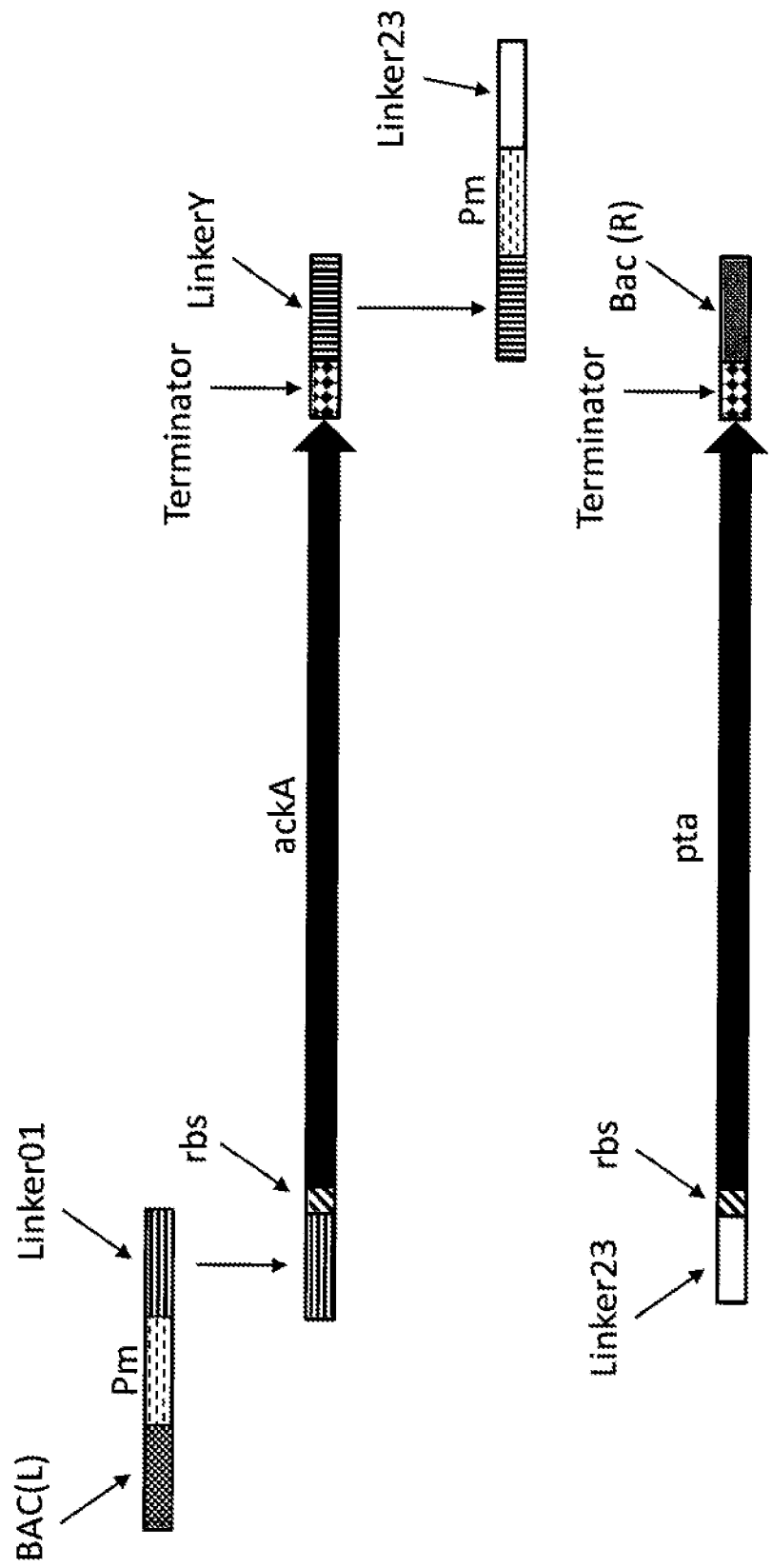
FIG. 8C is a schematic illustrating the assembly strategy for the nucleic acid fragments shown in FIG. 8B.

In order to construct the library, four different DNA fragments were required as well as a vector, requiring assembly of five DNA pieces in all. To each of the genes a ribosome binding site (rbs) and terminator sequences were added, as shown in FIG. 8C. Additionally, a linker (40 bp) was used to connect the genes with the promoter pieces. At both ends of the total insert, 40 bp overlapping sequences with the BAC vector (pCC1BAC linearized at EcoRI site, Epicentre) were used to enable the complete assembly.

All the synthetic nucleic acid portions (genes and promoters) were flanked by NotI sites and supplied as inserts in pUC57 plasmids. In order to release the pieces from the plasmids, a NotI restriction digest step was required before the isothermal T5 assembly step. The DNA in the NotI digest reaction consisted of 25 fmol of each of the promoter pieces (total of 8) and 20 fmol of each gene (total of 10). Also, the PCR amplified *E. coli* genes were added to the reaction (even though they were not cloned in plasmids) and did not contain NotI site and therefore were not affected by the digest. The NotI restriction digest reaction was carried out in 50 μL for one hour at 37° C. and contained the following: 28 μl of DNA, 15.5 μl of $H_2O$, 0.5 μl of BSA, 5 μl of buffer, and 1 μl of NotI.

Following one hour incubation at 37° C. the DNA was extracted with phenol-chloroform-isoamylalcohol and ethanol precipitated. The pellet was resuspended in the same initial volume of 28 μL. Then, the isothermal T5 exonuclease assembly reaction was conducted by incubating the following reagents at 50° C. for 30 minutes: 28 μl of pooled DNA (100 fmol of each of the 4 pooled pieces), 1.0 μl of pCC1BAC™ (100 fmol), 16 μl of 5×ISO buffer, 1.6 μl T5 exonuclease (0.2 U/μl, Epicentre), 8.0 μl of Taq DNA Ligase (40 U/μl, NEB), 1.0 μl of PHUSION® DNA Polymerase (2 U/μl, NEB), and 24.4 μl of $H_2O$, for a total 80 μl reaction.

Figure 8D:
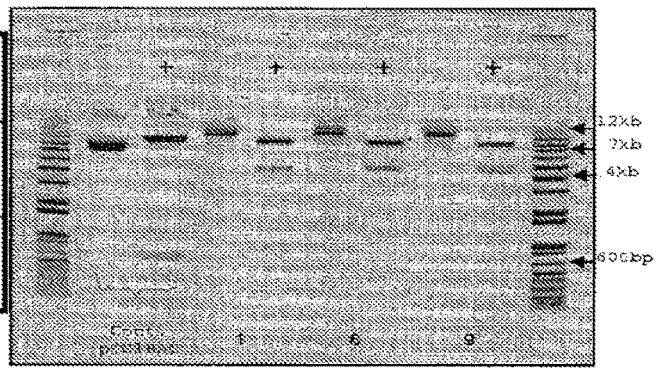
FIG. 8D shows the results of the assembly of an exemplary acetate utilization pathway as shown in FIG. 8C, showing assembly product released from the vector by restriction enzyme digest.

The DNA from the reaction was extracted with phenol-chloroform-isoamylalcohol and ethanol precipitated. Potential assembly products were visualized on 0.8% EtBr E-Gel. Standard procedures were used to transform *E. coli*, and strains that were not acetate inhibited and grew well on acetate as the sole carbon source were selected for. A triple *E. coli* mutant (Δacs ΔackA Δpta; deficient in acetate utilization and therefore does not grow on acetate substrate) was transformed with assembly reaction, whereby 20 μl of electro-competent cells were electroporated with 2 μl of the assembly reaction. The cells were plated on minimal medium agar plates containing 50 mM of acetate as a sole carbon source and chloramphenicol for selection, and incubated at 32° C. for 4 days. Resulting colonies were then analyzed to confirm the presence of the combinatorial assembly product (11,830 bp as compared to the plasmid control of 8,128 bp) as shown in FIG. 8D, and then sequence-verified. The triple mutant, which cannot grow on acetate was thus successfully transformed with a pACK-PTA combinatorially assembled construct.

Variants of the combinatorial constructs may then be screened for desirable properties, such as high production levels and efficient utilization of acetate.

Example XI

Assembly of a Complete Mouse Mitochondrial Genome Using the T5 Exonuclease One-Step Isothermal Method The methods of the present invention were used to assemble the complete mouse mitochondrial genome. This example shows the assembly of this genome, which has previously been difficult to construct due to its high A+T content of ~65%. The assembly was performed using an 8×60mer assembly method, i.e., eight 60 base oligonucleotides with 20 bp overlaps per micro titer well to assemble 300 bp per well, in 75 wells.

Briefly, 600 60 base oligonucleotides were synthesized to cover the entire mitochondrial genome, with appropriate 20 bp overlapping regions. 75 reactions of 8 oligonucleotides each were pooled at a per oligonucleotide concentration of 180 nM. The oligonucleotide pools were then diluted 1:4 with the assembly system components, and assembled with the T5 isothermal assembly method of the present invention for 1 hour at 50° C. in pUC19 vectors. NotI restriction sites, which flank each insert are produced following assembly since they are added to the terminal oligonucleotides in each set of 8 (e.g., oligo 1 and oligo 8), thus allowing the insert to be released from the vector prior to the next round of assembly. The 75 assembly reactions were then transformed into *E. coli* via electroporation for further analysis. All assemblies were sequence-verified. Products were amplified with PHUSION® polymerase to saturation (30 cycles, all 75 pieces between 35-45 ng/µl). 5 reactions were pooled and digested with NotI to remove non-complementary sequences.

Figure 9A:
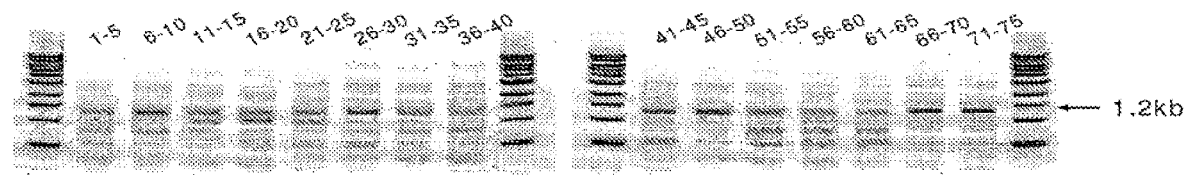
FIG. 9A-9F show the sequential assembly of a complete mouse mitochondrial genome using the method shown in FIG. 5A (T5 exonuclease).
Figure 9B:
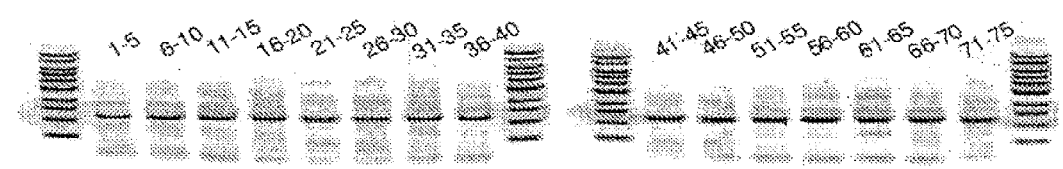

NotI digested reaction products of wells were then sequentially combined, first to form 1,180 bp fragments (five 300 bp fragments in 15 reactions). Pools of 5 reactions from the prior step were assembled as above in pBR322 vectors. AscI restriction sites, which flank each insert are produced following assembly since they were designed into the oligonucleotides that produce the terminal cassettes in each set of 5 (e.g., cassette 1 and cassette 5), thus allowing the insert to be released from the vector prior to the next round of assembly. (see FIG. 9A); and then amplified with PHUSION® polymerase to saturation (30 cycles, all 15 pieces between 45-70 ng/µl (see FIG. 9B). 5 reactions were pooled and digested with AscI to remove non-complementary sequences.

Figure 9C:
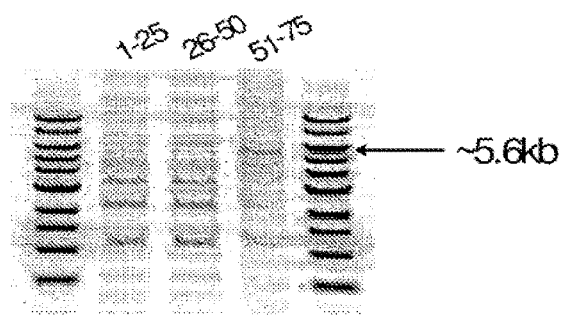
Figure 9D:
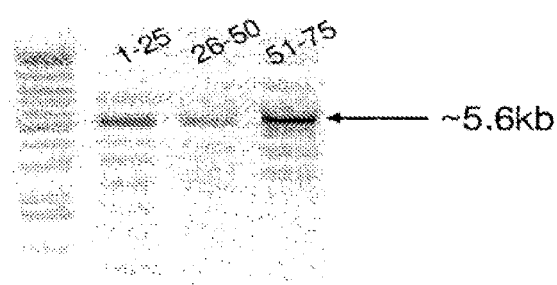

AscI digested reaction products were then combined to form 5,560 bp fragments (five 1,180 bp fragments in 3 reactions). Pools of 5 reactions from the prior step were assembled as above in pSmart-BAC vectors. SbfI restriction sites, which flank each insert are produced following assembly since they were designed into the oligonucleotides that produce the terminal cassettes in each set of 3 (e.g., cassette 1 and cassette 25), thus allowing the insert to be released from the vector prior to the next round of assembly. (see FIG. 9C); and then amplified with PHUSION® polymerase for 20-25 cycles (see FIG. 9D). 3 reactions were pooled and digested with SbfI to remove non-complementary sequences.

Figure 9E:
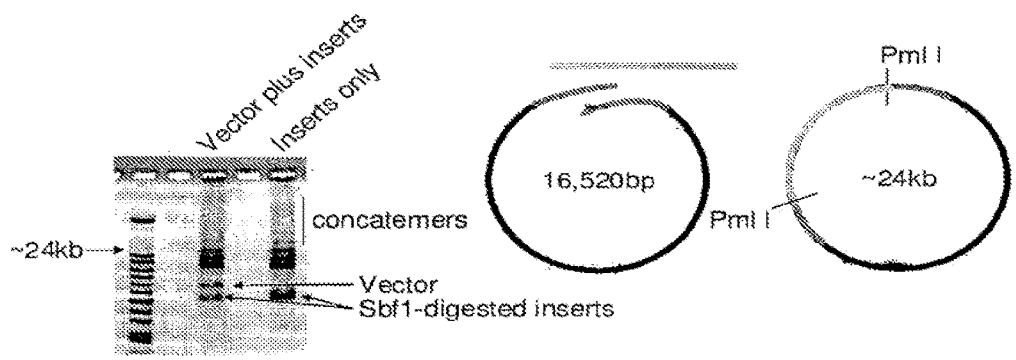

Final assembly of the whole mitochondrial genome of 16,520 bp was in pCC1BAC™ (FIG. 9E—three 5,560 bp fragments in 1 reaction) representing NC 005089 *M. musculus* mitochondrial genome (16,299 bp). The assembled genome was designed to contain an additional 221 bases (bases 1-221 are duplicated at the end of the sequence, see below) so the assembly product is therefore 16,520 bp and not 16,299 bp. Full-length sequence clones were then sequence-verified.

Figure 9F:
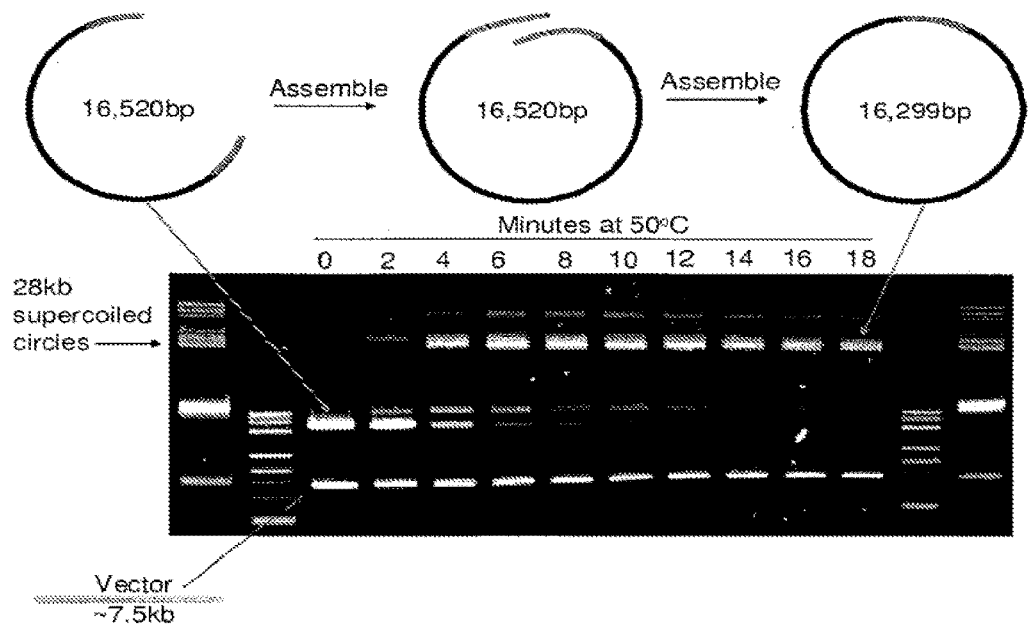

In order to produce a mitochondrial genome that was free from any vector sequence (i.e., exactly as found in nature) bases 1-221 were duplicated at the end of the 16,299 bp sequence (i.e., at bases 16,300 bp to 16,520 bp) to produce an assembled product size of 16,520 bp. Digestion with PmlI (designed into the oligonucleotides that produced cassettes 1 and 75) releases the vector sequence. This creates an overlap between the ends of the mitochondrial genome, which can then be joined by the T5 exonuclease isothermal assembly method (or the other assembly methods) as shown in FIG. 9F.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding specific embodiments are to be construed as merely illustrative, and not limiting of the scope of the invention in any way whatsoever. The entire disclosure of all applications, patents, publications (including reference manuals) cited above and in the figures, are hereby incorporated in their entirety by reference.

What is claimed is:

1. An in vitro method of joining a set of two or more double-stranded (ds) or single-stranded (ss) DNA molecules, wherein adjacent DNA molecules to be joined contain overlapping sequences at their termini, said method comprising contacting in vitro the two or more DNA molecules in a single vessel with
   (a) an isolated non-thermostable 5' to 3'exonuclease that lacks 3' exonuclease activity,
   (b) a crowding agent,
   (c) an isolated thermostable non-strand-displacing DNA polymerase with 3' exonuclease activity, or a mixture of said DNA polymerase with a second DNA polymerase that lacks 3' exonuclease activity,
   (d) an isolated thermostable ligase,
   (e) a mixture of dNTPs, and
   (f) a suitable buffer,
under conditions that are effective for joining the two or more DNA molecules to form a first assembled dsDNA molecule in a one-step reaction.

2. The method of claim 1, wherein the exonuclease of (a) is a T5 exonuclease and said contacting is under isothermal conditions.

3. The method of claim 1, wherein
   the crowding agent of (b) is PEG, and/or
   the non-strand-displacing DNA polymerase of (c) is PHUSION™ DNA polymerase or VENT® DNA polymerase, and/or the ligase of (d) is Taq ligase.

4. The method of claim 1, wherein the conditions are also suitable for digesting any unpaired, non-homologous, single-stranded DNAs following the joining reaction.

5. The method of claim 4, wherein at least some of the DNA molecules to be joined comprise, at one terminus, a sequence that is non-homologous to any of the DNA molecules of interest.

6. The method of claim 5, wherein the non-homologous sequences comprise one or more binding regions for PCR primers, and/or regions of homology to vector sequences, and/or recognition sites for one or more restriction enzymes.

7. The method of claim 1, further comprising repeating the method to join a second set of two or more DNA molecules to one another to obtain a second assembled DNA molecule, and then joining the first and the second assembled DNA molecules to obtain a third assembled ds DNA molecule.

8. A kit for a one-step in vitro reaction to join a set of two or more double-stranded (ds) or single-stranded (ss) DNA molecules, wherein adjacent DNA molecules to be joined contain overlapping sequences at their termini, comprising in a single vessel
   (a) an isolated non-thermostable 5' to 3'exonuclease that lacks 3' exonuclease activity,
   (b) a crowding agent,
   (c) an isolated thermostable non-strand-displacing DNA polymerase with 3' exonuclease activity, or a mixture of said DNA polymerase with a second DNA polymerase that lacks 3' exonuclease activity,
   (d) an isolated thermostable ligase,
   in amounts such that when said two or more DNA molecules are added to the kit, in the presence of a suitable buffer solution and dNTPs, and incubated under isothermal conditions, the two or more DNA molecules are assembled in a concerted reaction.

9. The kit of claim 8, comprising
   (a) T5 exonuclease;
   (b) PEG
   (c) Phusion™ DNA polymerase, and
   (d) Taq ligase.

10. A method of modifying the properties of a whole nucleic acid molecule, said method comprising:
   (a) representationally dividing the nucleic acid sequence of said whole nucleic acid molecule into a multiplicity of portions along its length thereby identifying the sequences of partial nucleic molecules;
   (b) providing, for at least 3 of said partial nucleic molecules, a multiplicity of variants of each partial nucleic acid molecule;
   (c) combinatorially assembling in vitro said variants along with any partial nucleic acid molecules which are not varied, wherein the partial nucleic acid molecules or variants thereof contain overlapping sequences at their termini whereby assembly of the partial nucleic acid molecules and variants thereof in the mixture would result in assembly of a multiplicity of variants of the whole nucleic acid molecule; and
   (d) expressing the variants of the whole nucleic acid molecule to determine any modified properties of said variants of said whole nucleic acid molecule; wherein the assembling of step (c) is performed by the method of claim 1.

11. An in vitro method of joining a set of two or more double-stranded (ds) or single-stranded (ss) DNA molecules, wherein adjacent DNA molecules to be joined contain overlapping sequences at their termini, said method comprising contacting in vitro the two or more DNA molecules in a single vessel with
   (a) an isolated non-thermostable 3' to 5' exonuclease active in the presence of dNTPs,
   (b) a crowding agent,
   (c) an isolated heat-activated DNA polymerase,
   (d) an isolated thermostable ligase,
   (e) a mixture of dNTPs, and
   (f) a suitable buffer,
   under conditions that are effective for joining the two or more DNA molecules to form a first assembled dsDNA molecule in a one-step thermocycled reaction.

12. The method of claim 11, wherein the exonuclease of (a) is Exonuclease III.

13. The method of claim 11, wherein polymerase of (c) is heat-activated by the removal of an inactivating moiety combined with the polymerase in a heat-sensitive manner.

14. The method of claim 11, wherein
   the crowding agent of (b) is PEG, and/or
   the DNA polymerase of (c) is AMPLITAQ GOLD®, and/or
   the ligase of (d) is Taq ligase.

15. The method of claim 11, further comprising repeating the method to join a second set of two or more DNA molecules to one another to obtain a second assembled DNA molecule, and then joining the first and the second assembled DNA molecules to obtain a third assembled ds DNA molecule.

16. A kit for a one-step in vitro reaction to join a set of two or more double-stranded (ds) or single-stranded (ss) DNA molecules, wherein adjacent DNA molecules to be joined contain overlapping sequences at their termini, comprising in a single vessel
   (a) an isolated non-thermostable 3' to 5' exonuclease active in the presence of dNTPs,
   (b) a crowding agent,
   (c) an isolated heat-activated DNA polymerase,
   (d) an isolated thermostable ligase,
   (e) a mixture of dNTPs, and
   (f) a suitable buffer,
   in amounts such that when said two or more DNA molecules are added to the kit, in the presence of a suitable buffer solution and dNTPs, and incubated under thermocycled conditions, the two or more DNA molecules are assembled in a concerted reaction.

17. A method of modifying the properties of a whole nucleic acid molecule, said method comprising:
   (a) representationally dividing the nucleic acid sequence of said whole nucleic acid molecule into a multiplicity of portions along its length thereby identifying the sequences of partial nucleic molecules;
   (b) providing, for at least 3 of said partial nucleic molecules, a multiplicity of variants of each partial nucleic acid molecule;
   (c) combinatorially assembling in vitro said variants along with any partial nucleic acid molecules which are not varied, wherein the partial nucleic acid molecules or variants thereof contain overlapping sequences at their termini whereby assembly of the partial nucleic acid molecules and variants thereof in the mixture would result in assembly of a multiplicity of variants of the whole nucleic acid molecule; and
   (d) expressing the variants of the whole nucleic acid molecule to determine any modified properties of said variants of said whole nucleic acid molecule; wherein the assembling of step (c) is performed by the method of claim 11.

18. A method of modifying the properties of a whole nucleic acid molecule, said method comprising:
   (a) representationally dividing the nucleic acid sequence of said whole nucleic acid molecule into at least 5 portions along its length thereby identifying the sequences of partial nucleic molecules;

(b) providing, for at least 3 of said partial nucleic molecules, a multiplicity of variants of the partial nucleic acid molecule;

(c) combinatorially assembling in vitro said variants along with any partial nucleic acid molecules which are not varied, wherein the partial nucleic acid molecules or variants thereof contain overlapping sequences at their termini whereby assembly of the partial nucleic acid molecules and variants thereof in the mixture would result in assembly of a multiplicity of variants of the whole nucleic acid molecule; and (d) expressing the variants of the whole nucleic acid molecule to determine any modified properties of the variants of said whole nucleic acid molecule.

19. The method of claim 18, wherein the variants of the partial nucleic acid molecule provide degenerate forms of the codon for one or more amino acids encoded by the partial nucleic acid molecules; or wherein the variants of the partial nucleic acid molecule provide a multiplicity of nucleic acid control sequences affecting transcliption or translation of the whole nucleic acid molecule; or wherein the variants of the partial nucleic acid molecule provide a multiplicity of regions encoding domains or motifs of peptides or proteins encoded by the whole nucleic acid molecule; or wherein the peptides or proteins encoded by said partial nucleic acid molecules function together in a metabolic pathway.

20. A method of modifying the properties of a whole nucleic acid molecule, said method comprising:

(a) representationally dividing the nucleic acid sequence of said whole nucleic acid molecule into a multiplicity of portions along its length thereby identifying the sequences of partial nucleic molecules;

(b) providing, for at least 3 of said partial nucleic molecules, a multiplicity of variants of the partial nucleic acid molecule;

(c) combinatorially assembling in vitro said variants along with any partial nucleic acid molecules which are not varied, wherein the partial nucleic acid molecules or variants thereof contain overlapping sequences at their termini whereby assembly of the partial nucleic acid molecules and variants thereof in the mixture would result in assembly of a multiplicity of variants of the whole nucleic acid molecule; and (d) expressing the variants of the whole nucleic acid molecule to determine any modified properties of the variants of said whole nucleic acid molecule;

wherein the variants of the partial nucleic acid molecule provide degenerate forms of the codon for one or more amino acids encoded by the partial nucleic acid molecules, or wherein the variants of the partial nucleic acid molecule provide a multiplicity of nucleic acid control sequences affecting transcription or translation of the whole nucleic acid molecule, or wherein the variants of the partial nucleic acid molecule provide a multiplicity of regions encoding domains or motifs of peptides or proteins encoded by the whole nucleic acid molecule, or wherein peptides or proteins encoded by said partial nucleic acid molecules function together in a metabolic pathway.

* * * * *

SEQUENCE LISTING

```
Sequence total quantity: 16
SEQ ID NO: 1            moltype = DNA  length = 40
FEATURE                 Location/Qualifiers
misc_feature            1..40
                        note = Forward primer for F1 Fragment of Clostridium
                         cellulolyticumgenomic DNA
source                  1..40
                        mol_type = other DNA
                        organism = synthetic construct
SEQUENCE: 1
gcagcttcaa gtcctgcaaa caaggtgtac caggatcgtt                                       40

SEQ ID NO: 2            moltype = DNA  length = 40
FEATURE                 Location/Qualifiers
misc_feature            1..40
                        note = Reverse primer for F1 Fragment of Clostridium
                         cellulolyticumgenomic DNA
source                  1..40
                        mol_type = other DNA
                        organism = synthetic construct
SEQUENCE: 2
gatttcagtg tagttagggc cagttgaatt caaacctgcc                                       40

SEQ ID NO: 3            moltype = DNA  length = 40
FEATURE                 Location/Qualifiers
misc_feature            1..40
                        note = Forward primer for F2 Fragment of Clostridium
                         cellulolyticumgenomic DNA
source                  1..40
                        mol_type = other DNA
                        organism = synthetic construct
SEQUENCE: 3
ggcaggtttg aattcaactg gccctaacta cactgaaatc                                       40

SEQ ID NO: 4            moltype = DNA  length = 40
FEATURE                 Location/Qualifiers
misc_feature            1..40
                        note = Reverse primer for F2 Fragment of Clostridium
```

```
                          cellulolyticumgenomic DNA
source                   1..40
                         mol_type = other DNA
                         organism = synthetic construct
SEQUENCE: 4
cttggtgcca tcagcattgt tctctgtacc gcccactgtc                        40

SEQ ID NO: 5             moltype = DNA  length = 40
FEATURE                  Location/Qualifiers
misc_feature             1..40
                         note = Forward primer for F3 Fragment of Clostridium
                          cellulolyticumgenomic DNA
source                   1..40
                         mol_type = other DNA
                         organism = synthetic construct
SEQUENCE: 5
gacagtgggc ggtacagaga acaatgctga tggcaccaag                        40

SEQ ID NO: 6             moltype = DNA  length = 40
FEATURE                  Location/Qualifiers
misc_feature             1..40
                         note = Reverse primer for F3 Fragment of Clostridium
                          cellulolyticumgenomic DNA
source                   1..40
                         mol_type = other DNA
                         organism = synthetic construct
SEQUENCE: 6
cagttgaata atcatgtgtt cctgcggcaa atgcagtacc                        40

SEQ ID NO: 7             moltype = DNA  length = 40
FEATURE                  Location/Qualifiers
misc_feature             1..40
                         note = Forward primer for F4 Fragment of Clostridium
                          cellulolyticumgenomic DNA
source                   1..40
                         mol_type = other DNA
                         organism = synthetic construct
SEQUENCE: 7
ggtactgcat ttgccgcagg aacacatgat tattcaactg                        40

SEQ ID NO: 8             moltype = DNA  length = 40
FEATURE                  Location/Qualifiers
misc_feature             1..40
                         note = Reverse primer for F4 Fragment of Clostridium
                          cellulolyticumgenomic DNA
source                   1..40
                         mol_type = other DNA
                         organism = synthetic construct
SEQUENCE: 8
ttatttacca agaacctttg cctttaacat tgcaaagtca                        40

SEQ ID NO: 9             moltype = DNA  length = 39
FEATURE                  Location/Qualifiers
misc_feature             1..39
                         note = Forward primer for F5 Fragment of Mycoplasma
                          gallisepticumgenomic DNA
source                   1..39
                         mol_type = other DNA
                         organism = synthetic construct
SEQUENCE: 9
gcttgcatgc atcctgttta ttcatcacaa acattgaac                         39

SEQ ID NO: 10            moltype = DNA  length = 47
FEATURE                  Location/Qualifiers
misc_feature             1..47
                         note = Reverse primer for F5 Fragment of Mycoplasma
                          gallisepticumgenomic DNA
source                   1..47
                         mol_type = other DNA
                         organism = synthetic construct
SEQUENCE: 10
aattctgcag tttttatttc ctaacagaac attttttcta gtatagc                47

SEQ ID NO: 11            moltype = DNA  length = 39
FEATURE                  Location/Qualifiers
misc_feature             1..39
                         note = Forward primer for F7 Fragment of Mycoplasma
                          gallisepticumgenomic DNA
source                   1..39
```

```
                        mol_type = other DNA
                        organism = synthetic construct
SEQUENCE: 11
cgactctaga taaatagcct ttctttatct ttttgaggc                              39

SEQ ID NO: 12           moltype = DNA  length = 39
FEATURE                 Location/Qualifiers
misc_feature            1..39
                        note = Reverse primer for F7 Fragment of Mycoplasma
                         gallisepticumgenomic DNA
source                  1..39
                        mol_type = other DNA
                        organism = synthetic construct
SEQUENCE: 12
ccggggatcc ctttctcaat tgtctgctcc atatatgtt                              39

SEQ ID NO: 13           moltype = DNA  length = 62
FEATURE                 Location/Qualifiers
misc_feature            1..62
                        note = Forward primer for F6 Fragment of pRST21
source                  1..62
                        mol_type = other DNA
                        organism = synthetic construct
SEQUENCE: 13
tagaaaaat gttctgttag gaaataaaaa ctgcagaatt aaaagttagt gaacaagaaa        60
ac                                                                     62

SEQ ID NO: 14           moltype = DNA  length = 56
FEATURE                 Location/Qualifiers
misc_feature            1..56
                        note = Reverse primer for F6 Fragment of pRST21
source                  1..56
                        mol_type = other DNA
                        organism = synthetic construct
SEQUENCE: 14
agcctcaaaa agataaagaa aggctattta tctagagtcg acctgcagtt cagatc           56

SEQ ID NO: 15           moltype = DNA  length = 55
FEATURE                 Location/Qualifiers
misc_feature            1..55
                        note = Forward primer for F8 Fragment of pRST21
source                  1..55
                        mol_type = other DNA
                        organism = synthetic construct
SEQUENCE: 15
tgttcaatgt ttgtgatgaa taaacaggat gcatgcaagc ttttgttccc tttag            55

SEQ ID NO: 16           moltype = DNA  length = 51
FEATURE                 Location/Qualifiers
misc_feature            1..51
                        note = Reverse primer for F8 Fragment of pRST21
source                  1..51
                        mol_type = other DNA
                        organism = synthetic construct
SEQUENCE: 16
aaacatatat ggagcagaca attgagaaag ggatccccgg gtaccgagct c                51
```